(12) United States Patent
Ujibashi et al.

(10) Patent No.: US 10,783,983 B2
(45) Date of Patent: Sep. 22, 2020

(54) VARIANT INFORMATION PROCESSING DEVICE AND METHOD

(71) Applicant: FUJITSU LIMITED, Kawasaki-shi, Kanagawa (JP)

(72) Inventors: Yoshifumi Ujibashi, Kawasaki (JP); Motoyuki Kawaba, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 759 days.

(21) Appl. No.: 15/428,440

(22) Filed: Feb. 9, 2017

(65) Prior Publication Data
US 2017/0242588 A1 Aug. 24, 2017

(30) Foreign Application Priority Data

Feb. 19, 2016 (JP) .................... 2016-030268

(51) Int. Cl.
| | |
|---|---|
| G16B 20/20 | (2019.01) |
| G06F 16/22 | (2019.01) |
| G16B 20/00 | (2019.01) |
| G16B 50/00 | (2019.01) |
| G06F 3/06 | (2006.01) |

(52) U.S. Cl.
CPC .......... *G16B 20/20* (2019.02); *G06F 3/0604* (2013.01); *G06F 3/0655* (2013.01); *G06F 3/0673* (2013.01); *G06F 16/221* (2019.01); *G16B 20/00* (2019.02); *G16B 50/00* (2019.02)

(58) Field of Classification Search
None
See application file for complete search history.

(56) References Cited

U.S. PATENT DOCUMENTS

| | | | |
|---|---|---|---|
| 2014/0280327 A1* | 9/2014 | Pham ................. | G16B 20/20 707/770 |
| 2014/0310215 A1* | 10/2014 | Trakadis .............. | G16B 20/00 706/13 |
| 2016/0048633 A1* | 2/2016 | Pham ................ | G06F 16/9024 707/737 |

OTHER PUBLICATIONS

Umadevi Paila et al., "GEMINI: Integrative Exploration of Genetic Variation and Genome Annotations", PLOS Computational Biology, vol. 9, Issue 7, e1003153, pp. 1-8, Jul. 2013 [online], [retrieved Feb. 1, 2016], Internet <URL: http://journals.plos.org/ploscompbiol/article?ID=10.1371/journal.pcbi.1003153>.

* cited by examiner

*Primary Examiner* — Olivia M. Wise
(74) *Attorney, Agent, or Firm* — Staas & Halsey LLP

(57) ABSTRACT

A variant information processing device for processing genetic information includes a processor configured to create variant storage data, from variant information of each of a plurality of target individuals to be processed, where the variant information includes information of variant locus and variant pattern associated with the variant locus. The variant locus corresponds to a portion where the genetic information varies among the plurality of target individuals, the variant pattern corresponds to the genetic information of the portion, and the variant storage data includes an array region with each a first storage region with a fixed bit length and a second storage region with the fixed bit length. The code associated with the variant pattern at each of the variant locus is stored in first storage region or both of the first and second storage regions depending on the length of variant pattern associated with the code.

19 Claims, 20 Drawing Sheets

FIG. 2

|  | VARIANT LOCUS 0 | VARIANT LOCUS 1 | VARIANT LOCUS 2 | VARIANT LOCUS 3 | VARIANT LOCUS 4 | VARIANT LOCUS 5 | ... | VARIANT LOCUS N-1 |
|---|---|---|---|---|---|---|---|---|
| INDIVIDUAL 0 | A/A | A/C | G/G | C/G | C/T | T/T | ... | C/G (VARIANT PATTERN) |
| INDIVIDUAL 1 | A/A | A/C | C/G | C/G | T/T | A/T | ... | G/G |
| INDIVIDUAL 2 | A/A | A/C | G/G | C/G | T/T | A/T | ... | G/G |
| INDIVIDUAL 3 | A/C | A/C | C/C | C/G | T/T | A/T | ... | C/G |
| ... | | | | | | | | |

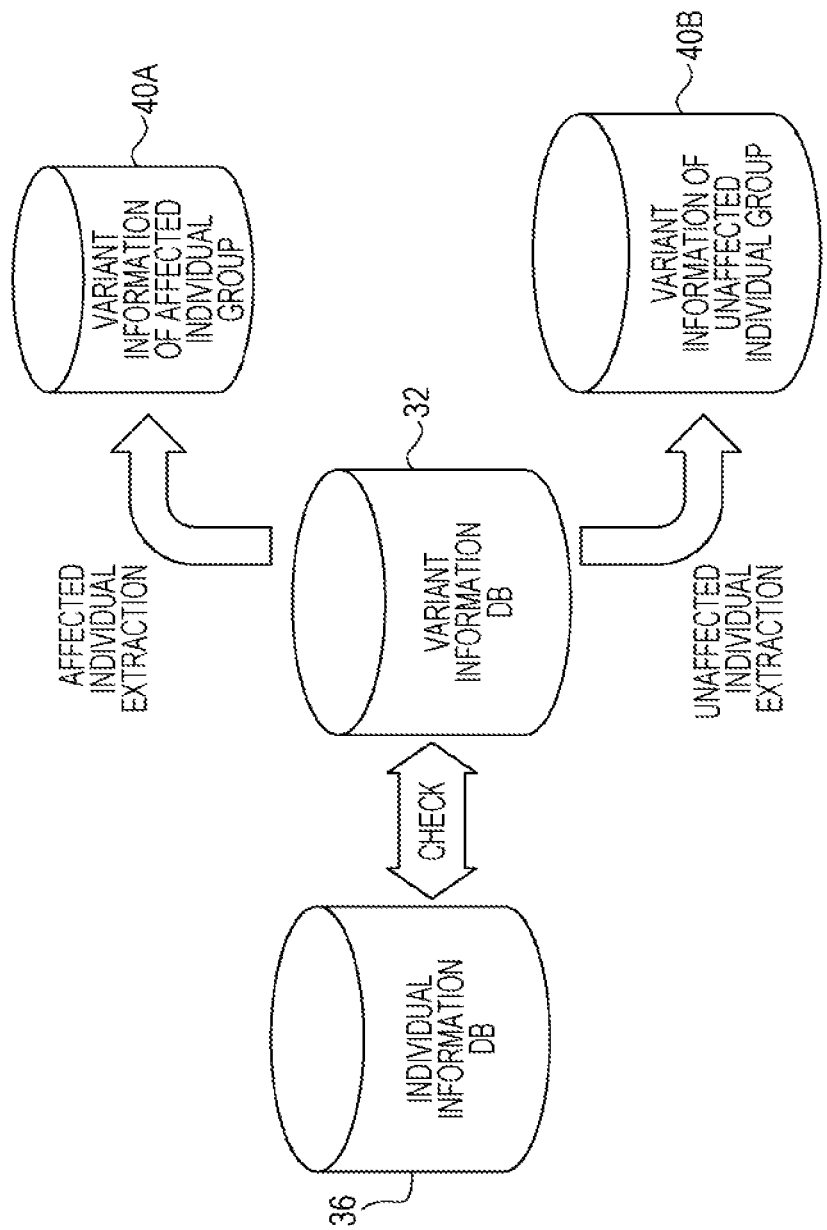

FIG. 4

| | | | | |
|---|---|---|---|---|
| VARIANT LOCUS 0 | VARIANT PATTERN (INDIVIDUAL 0) | VARIANT PATTERN (INDIVIDUAL 1) | VARIANT PATTERN (INDIVIDUAL 2) ... | VARIANT PATTERN (INDIVIDUAL M-1) |
| VARIANT LOCUS 1 | VARIANT PATTERN (INDIVIDUAL 0) | VARIANT PATTERN (INDIVIDUAL 1) | VARIANT PATTERN (INDIVIDUAL 2) ... | VARIANT PATTERN (INDIVIDUAL M-1) |
| VARIANT LOCUS 2 | VARIANT PATTERN (INDIVIDUAL 0) | VARIANT PATTERN (INDIVIDUAL 1) | VARIANT PATTERN (INDIVIDUAL 2) ... | VARIANT PATTERN (INDIVIDUAL M-1) |
| ... | | | | |
| VARIANT LOCUS N-1 | VARIANT PATTERN (INDIVIDUAL 0) | VARIANT PATTERN (INDIVIDUAL 1) | VARIANT PATTERN (INDIVIDUAL 2) ... | VARIANT PATTERN (INDIVIDUAL M-1) |

48

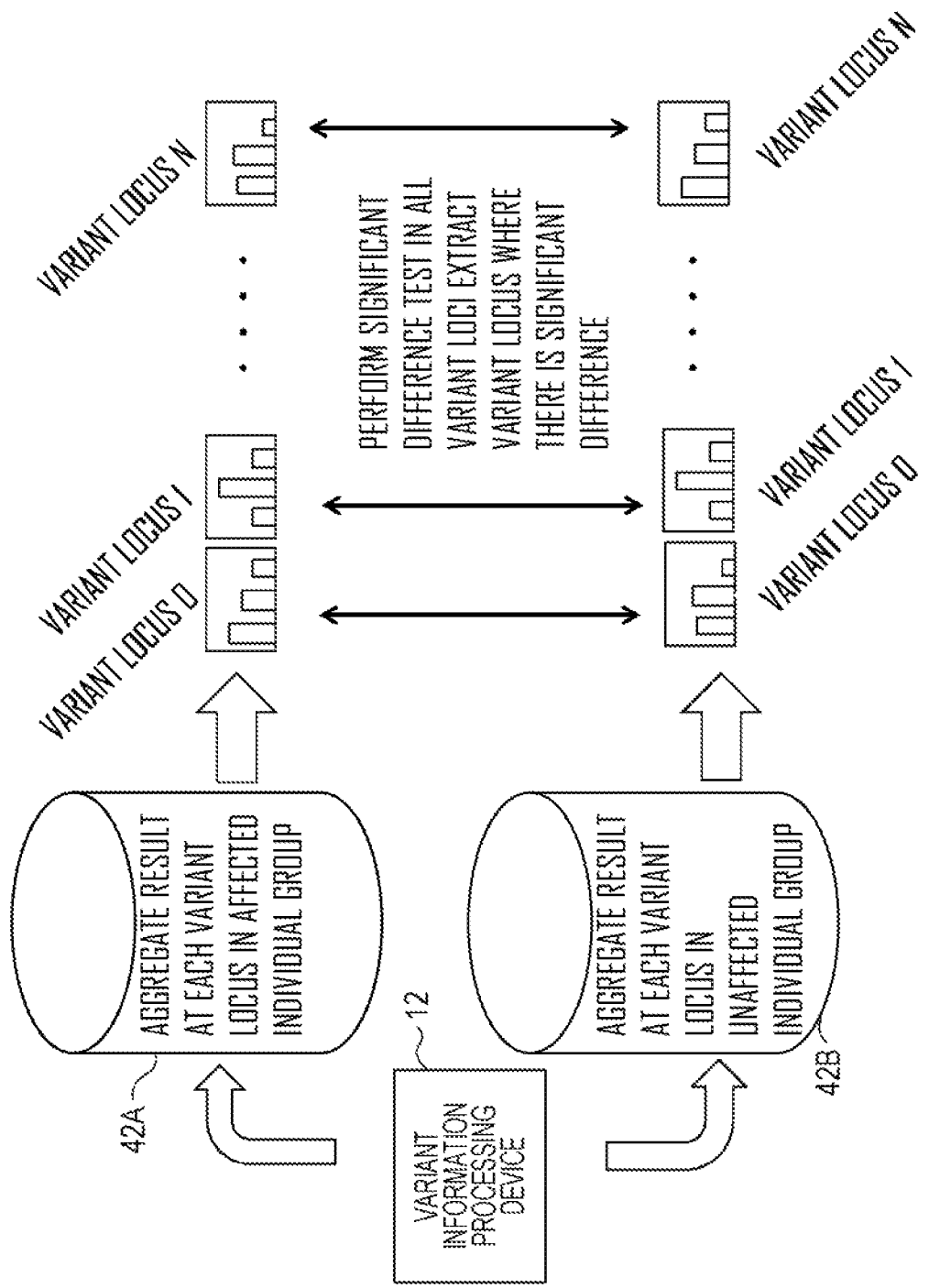

FIG. 6
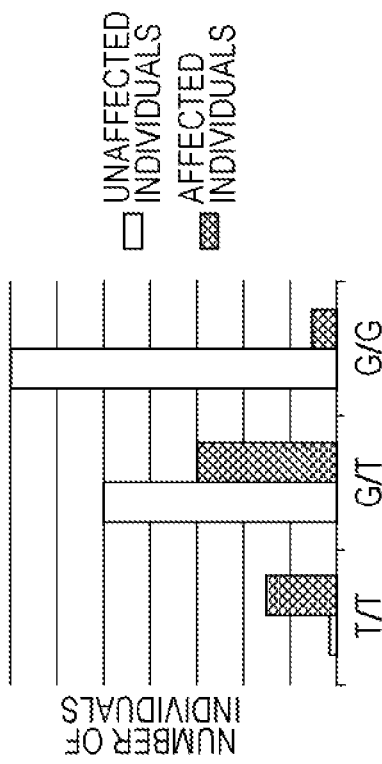
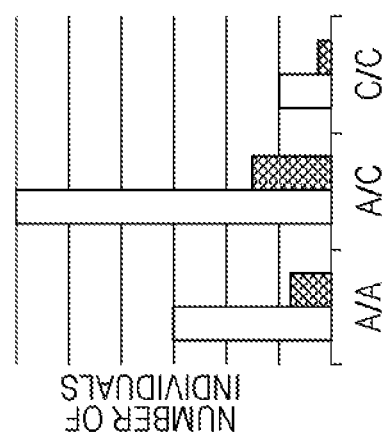

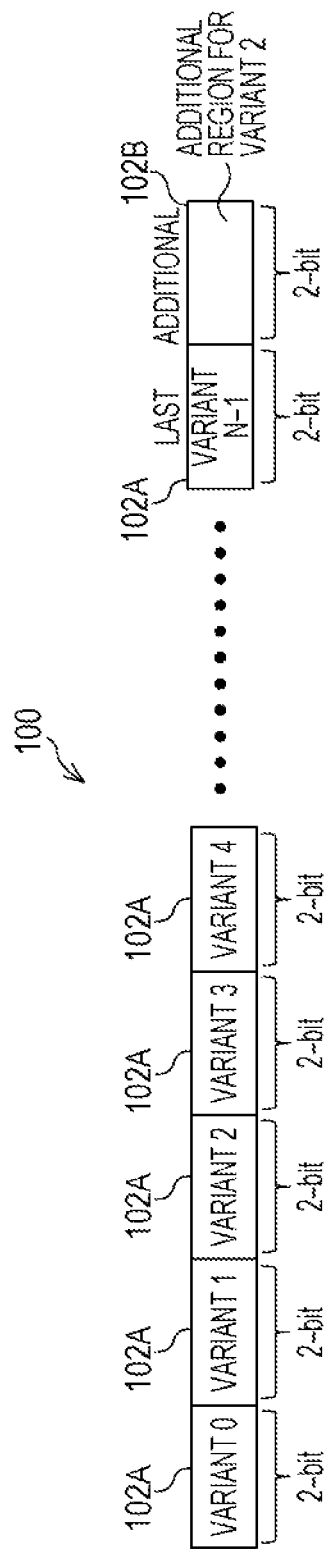

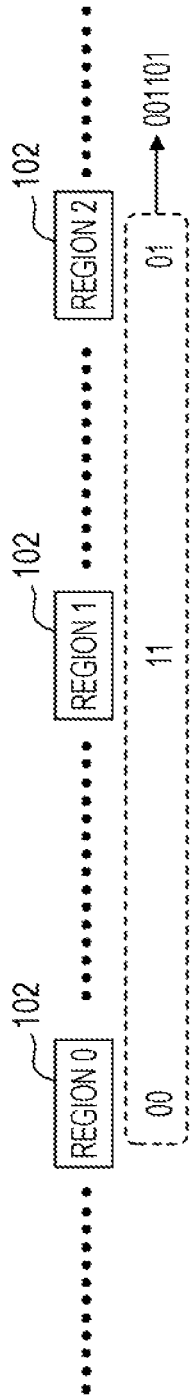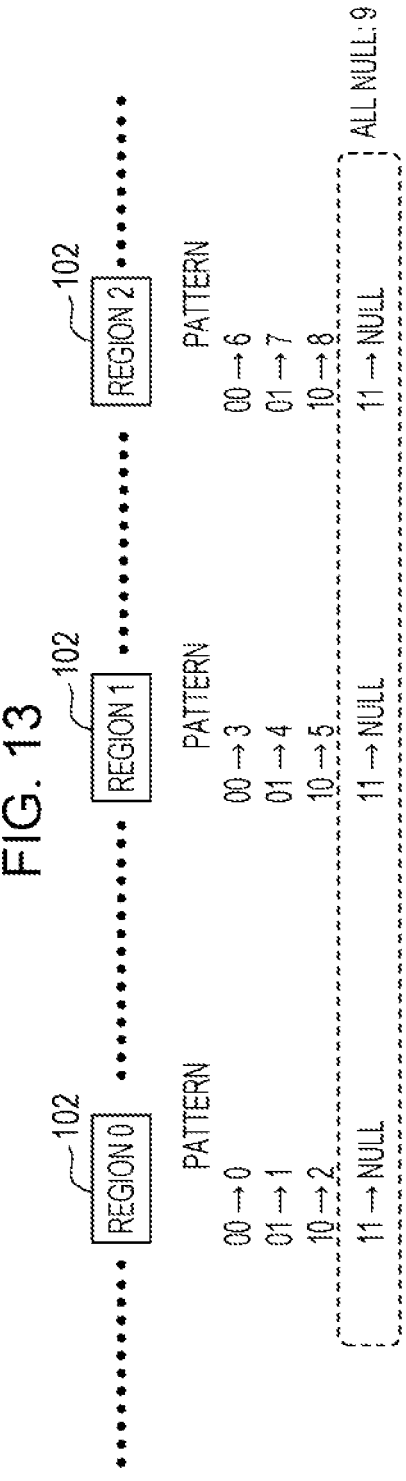

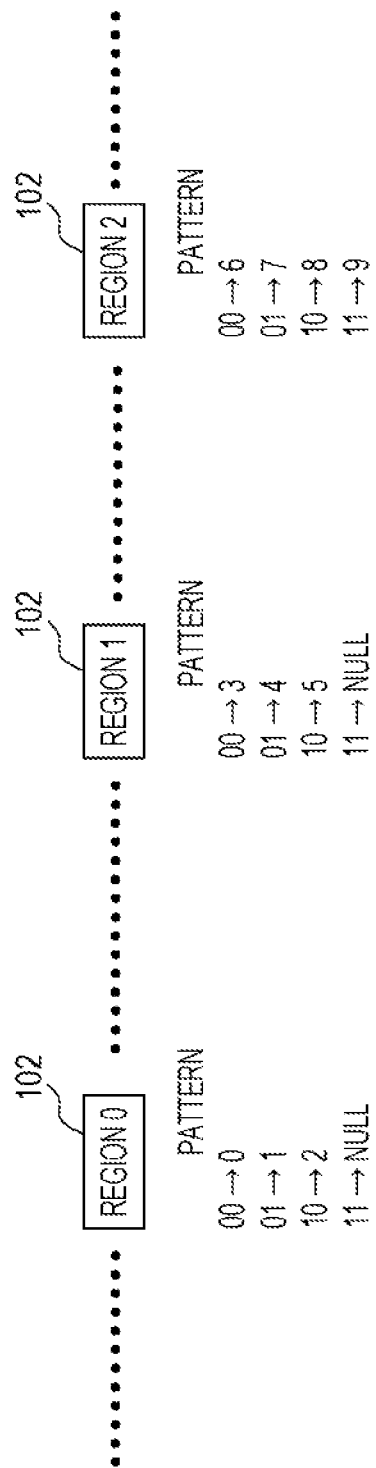

VARIANT INFORMATION PROCESSING DEVICE AND METHOD

CROSS-REFERENCE TO RELATED APPLICATION

This application is based upon and claims the benefit of priority of the prior Japanese Patent Application No. 2016-030268, filed on Feb. 19, 2016, the entire contents of which are incorporated herein by reference.

FIELD

The embodiments discussed herein are related to a variant information processing device, a variant information processing method, and a non-transitory computer-readable recording medium having stored therein a program for causing a computer to execute a process for variant information.

BACKGROUND

In genetic information (base sequences of DNA), there are several tens of millions of portions which cause individual variability, that is, portions where the genetic information varies among individuals (these portions are referred to as variant loci). The genetic information (variant patterns) in one or some of these variant loci may be correlated to occurrence of a specific disease. Accordingly, there has been developed a research for analyzing the variant locus correlated to the occurrence of the disease and a variant pattern at this variant locus in a way such as to test on each variant locus whether there is significant difference in frequency of appearance of a variant pattern between a group of individuals affected by a target disease and a group of individuals unaffected by the target disease.

In relation to this, there has been proposed a technique in which the variant patterns at the respective variant loci in one individual are obtained from a variant call format (VCF) file storing the variant patterns of multiple individuals at the variant loci, and are stored in an individual column of a database together with related annotations.

Such a technique is described in, for example, Umadevi Paila, Brad A. Chapman, Rory Kirchner, Aaron R. Quinlan, "GEMINI: Integrative Exploration of Genetic Variation and Genome Annotations", [online], [retrieved Feb. 1, 2016], Internet <URL: journals.plos.org/ploscompbiol/article?ID=10.1371/journal.pcbi.1003153>.

SUMMARY

According to an aspect of the invention, a variant information processing device for processing genetic information of a plurality of individuals includes a processor configured to create variant storage data, from variant information of each of a plurality of target individuals to be processed, the variant information including information of variant locus and variant pattern associated with the variant locus, the variant locus corresponding to a portion where the genetic information varies among the plurality of target individuals, the variant pattern corresponding to the genetic information of the portion, the variant storage data including an array region with each a first storage region with a fixed bit length and a second storage region with the fixed bit length, a first variant locus being the variant locus, the number r of the variant patterns associated with the variant locus being equal to or smaller than the number s of types of codes, each of the codes being associated with a corresponding one of the variant patterns and being able to be stored in the first storage region, a second variant locus being the variant locus, the number r of the variant patterns associated with the variant locus being greater than the number s, the code associated with the variant pattern of the first variant locus being stored in the first storage region associated with the first variant locus, and the code associated with the variant pattern of the second variant locus being stored in a specific storage region selected from between the first storage region associated with the second variant locus and the second storage region, a certain code being stored, except the specific storage region, in the first storage region associated with the second variant locus or the second storage region.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 2 is a schematic diagram illustrating an example of variant information of each of individuals stored in a variant information DB;

FIG. 3 is a conceptual diagram illustrating an outline of a process by a variant information extraction device;

FIG. 4 is a schematic diagram illustrating part of a VCF file which is an example of the variant information inputted into a variant information processing device;

FIG. 5 is a conceptual diagram illustrating an outline of a process by an aggregate result processing device;

FIG. 6 is a conceptual diagram illustrating examples of distributions of variant patterns at a variant locus with no specificity and at a variant locus with specificity;

FIG. 10 is a schematic diagram illustrating a format of variant storage data;

FIG. 11 is a table illustrating an example of a variant master table;

FIG. 12 is a schematic diagram illustrating an example of a code indicating a variant pattern;

FIG. 13 is a schematic diagram illustrating an example of codes in the first embodiment;

FIG. 14 is a table illustrating an example of a correlation between pattern numbers of the variant patterns and the codes in the first embodiment;

FIG. 20 is a schematic diagram illustrating an example of codes in the second embodiment;

FIG. 21 is a table illustrating an example of the correlation between the pattern numbers of the variant patterns and the codes in the second embodiment;

DESCRIPTION OF EMBODIMENTS

The analysis of a variant locus correlated with occurrence of a specific disease inevitably involves an aggregate processing of counting how many times each variant pattern appears at each variant locus in all multiple individuals.

For example, when the database in the aforementioned technique is used, the aggregate processing may be achieved by repeating, for all columns (all target individuals to be processed), a process of obtaining information from one column and incrementing the count value of a variant pattern at each variant locus based on the obtained information.

Figure 24:
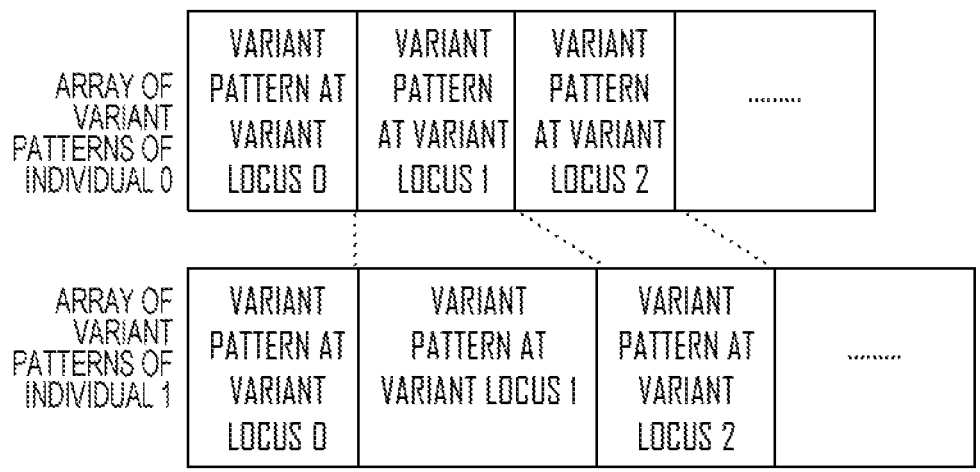
FIG. 24 is a schematic diagram for explaining problems in the case of using a conventional technique.

The length of region needed to store the expression of each variant pattern in each of the variant loci in the genetic information is the same in most of the individuals. However, in some individuals, the variant pattern varies such that, for example, the length of a certain variant pattern is longer than the standard length or no variant pattern exists (length 0). Accordingly, as one example illustrated in FIG. 24, the length expressing each variant pattern at the variant loci differs depending on the individuals. The example in FIG. 24 illustrates the difference in the lengths of the variant patterns for the variant locus 1 between the individuals 1 and 2.

Accordingly, when the aggregate processing is performed by using the array of variant patterns in each individual, the length of the variant pattern at each variant locus in each individual (each array) has to be determined and the aggregate processing takes quite long time although depending on the number of individuals to be processed.

Figure 25:
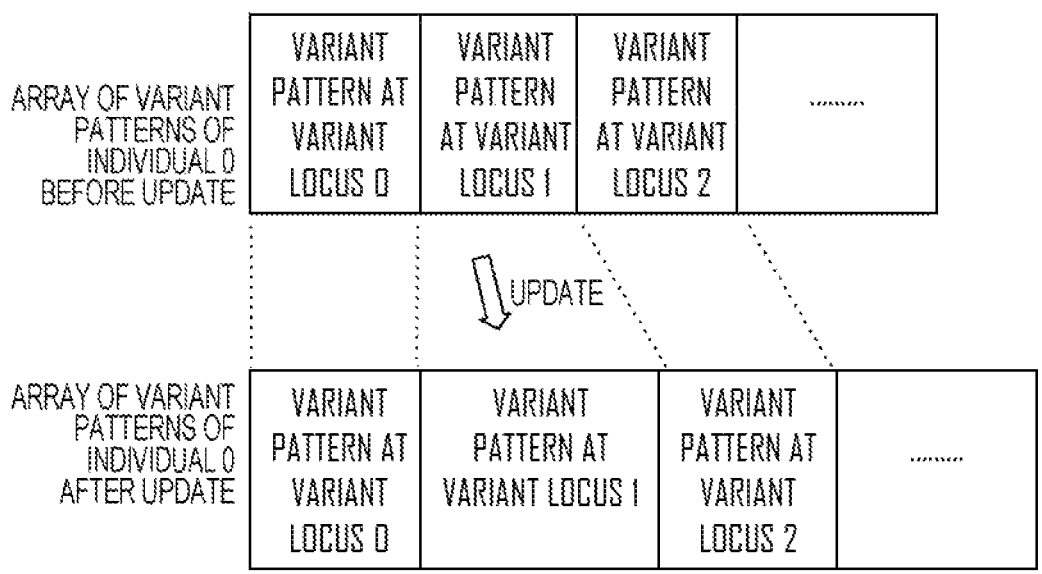
FIG. 25 is a schematic diagram for explaining problems in the case of using a conventional technique.

In another method, it is conceivable to perform a pre-process of converting the arrays of variant patterns in the individuals such that the length of information indicating the variant pattern at each variant locus is equalized, that is, setting the length of information indicating the variant pattern to a length capable of storing the longest variant pattern at each variant locus. As an example, FIG. 25 illustrates the case where the length of information indicating the variant pattern at the variant locus 1 in the array of variant patterns in the individual 0 is equalized to the length of information indicating the variant pattern at the variant locus 1 in the array of variant patterns in the individual 1. However, this pre-process also takes long processing time because the length of the longest variant pattern at each variant locus has to be obtained and the arrays of variant patterns in all individuals have to be converted according to the obtained length of the longest variant pattern.

An object of one aspect of the disclosed embodiments is to increase the speed of a processing of aggregating how many times each variant pattern appears at each variant locus in genetic information.

Examples of embodiments of a disclosed technique are described below in detail with reference to the drawings.

Embodiment 1

Figure 1:
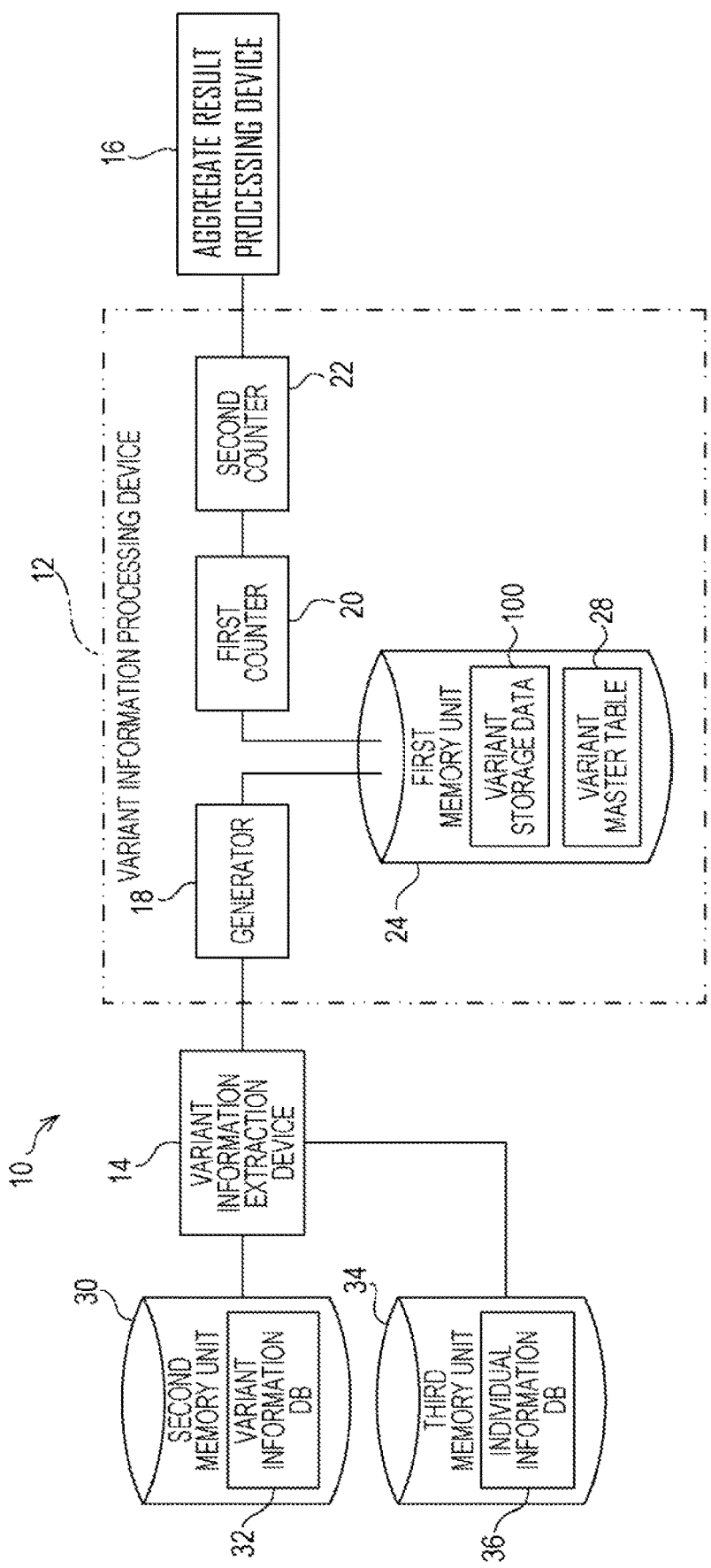
FIG. 1 is a schematic block diagram of a variant information analysis support system.

FIG. 1 illustrates a variant information analysis support system 10. The variant information analysis support system 10 includes a variant information processing device 12 which is an example of a variant information processing device in the disclosed technique, a variant information extraction device 14, and an aggregate result processing device 16.

The variant information extraction device 14 includes a second memory unit 30 storing a variant information database (DB) 32 and a third memory unit 34 storing an individual information DB 36. In the variant information DB 32, pieces of individual variant information of many individuals are registered in association with individual identifiers (IDs), respectively. As illustrated in FIG. 2 as an example, the individual variant information is information in which variant patterns at variant loci are extracted from individual genetic information and arranged in order. Note that, instead of the individual variant information, the entire individual genetic information may be stored in the DB. Note that the DB in the embodiments indicating the individual variant information as illustrated in FIG. 2 includes each of the columns which includes the variant patterns of the individuals with respect to corresponding one of the variant loci.

In the individual information DB 36, pieces of individual attribute information of the many individuals whose individual variant information is stored in the variant information DB 32 are registered. The individual attribute information includes at least the individual ID and information indicating presence or absence of a disease affecting the individual and, when the individual is affected by a disease, information indicating the disease. The individual attribute information may further include information on the sex, age, height, weight, lifestyle (for example, having or not of smoking habit and the like) and the like with respect to the individual.

When the variant information is to be analyzed, the variant information extraction device 14 receives at least information specifying a disease to be analyzed, as an extraction condition of the variant information. Moreover, extraction conditions such as sex, age, and the like are sometimes added. As illustrated in FIG. 3, upon receiving the extraction conditions, the variant information extraction device 14 checks the variant information DB 32 and the individual information DB 36 against each other and reads the individual variant information of an individual group matching the received extraction conditions from the variant information DB 32. The individual group whose individual variant information is read in this case is a set of individuals who are affected by at least the disease to be analyzed and is referred to as "affected individual group" in the following description. Then, the variant information extraction device 14 edits the read individual variant information into a predetermined format and outputs the edited individual variant information to the variant information processing device 12 as the variant information 40A of the affected individual group.

Moreover, the variant information extraction device 14 reads the individual variant information of an individual group which does not match the received extraction conditions or an individual group which partially matches the extraction conditions other than the diseases, from the variant information DB 32. The individual group whose individual variant information is read in this case is a set of individuals who are not affected by at least the disease to be analyzed and is referred to as "unaffected individual group" in the following description. Then, the variant information extraction device 14 edits the read individual variant information into the predetermined format and outputs the edited individual variant information as the variant information 40B of the unaffected individual group.

A variant call format (VCF) is given as an example of the aforementioned predetermined format. As illustrated in FIG. 4, a VCF file 48 includes information with a format in which the variant patterns of all individuals to be processed (all individuals in the affected individual group or the unaffected individual group in the embodiment) at each of the variant loci are arranged in order. The VCF is a common format as the format of the variant information and hereafter description is given of a mode in which the variant information extraction device 14 outputs the VCF files 48 as the variant information 40A of the affected individual group and the variant information 40B of the unaffected individual group. Note that the format of the variant information inputted into the variant information processing device 12 is not limited to the VCF and may be another format.

As illustrated in FIG. 1, the variant information processing device 12 includes a generator 18, a first aggregator 20, a second aggregator 22, and a first memory unit 24 storing variant storage data 100 and a variant master table 28. The generator 18, the first aggregator 20, and the second aggregator 22 perform the following processes on the variant information 40A of the affected individual group and the variant information 40B of the unaffected individual group which are targets of the processes and which are received from the variant information extraction device 14.

The generator 18 generates the variant storage data 100 including multiple storage regions with a fixed bit length, for each individual from the variant information received from the variant information extraction device 14, and stores the generated variant storage data 100 of each individual in the first memory unit 24. In the embodiment, the bit length of each storage region is 2 bits and the number s of types of codes storable in the storage region is four ($(00)_B$, $(01)_B$, $(10)_B$, and $(11)_B$, where $(x)_B$ represents that x is expressed in binary).

The generator 18 generates the variant storage data while switching the process as follows depending on whether each of the variant loci is a first variant locus or a second variant locus, the first variant locus being a site where the number r of types of variant patterns in all target individuals to be processed is equal to or smaller than the number s of types of codes which is four, the second variant locus being a site where the number r is greater than the number s of the types of codes which is four. Specifically, for the first variant locus, the generator 18 stores a code corresponding to the variant pattern at the first variant locus, in a storage region for the first variant locus in an array of storage regions for the respective variant loci. For the second variant locus, the generator 18 divides a group of a storage region for the second variant locus into a specific storage region having a bit length same to the storage region for the first variant locus and a storage region added behind the array including the storage regions for the first variant loci and the specific storage region. Then, the generator 18 stores a code corresponding to the variant pattern at the second variant locus in the specific storage region and stores a certain code in the rest of the storage regions. Moreover, the generator 18 generates the variant storage data 100 and the variant master table 28 and stores the generated variant master table 28 in the first memory unit 24.

The first aggregator 20 reads the variant storage data 100 of each individual generated by the generator 18 from the first memory unit 24, and aggregates how many times each of codes stored in each of the storage regions in the variant storage data 100 appears in all target individuals to be processed with respect to each storage region and each code. The aggregate results by the first aggregator 20 are stored in a temporal aggregate table (described later).

The second aggregator 22 aggregates, from the aggregate results in the storage regions obtained by the first aggregator 20, how many times each of types of variant patterns in all target individuals to be processed appears at each of the variant loci based on the variant master table 28 stored in the first memory unit 24. The aggregate results by the second aggregator 22 are stored in a final aggregate table (described later). The second aggregator 22 outputs the aggregate result stored in the final aggregate table to the aggregate result processing device 16.

As described above, the variant information processing device 12 performs the processes on the variant information 40A of the affected individual group and the variant information 40B of the unaffected individual group which are the targets of processes. Accordingly, as illustrated in FIG. 5 as an example, the variant information processing device 12 outputs an aggregate result 42A at each variant locus in the affected individual group and an aggregate result 42B at each variant locus in the unaffected individual group, and these aggregate results 42A and 42B are inputted into the aggregate result processing device 16.

The aggregate result processing device 16 tests whether there is a significant difference in frequency of appearance of each variant pattern at each variant locus between the affected individual group and the unaffected individual group, based on the received aggregate results 42A and 42B, by statistical methods such as the chi-squared test. The frequency of appearance of each variant pattern indicates distribution of the number of times of appearance of each variant pattern. For example, as illustrated in FIG. 6 as "example of variant distribution without specificity", at a variant locus where the distribution of the number of times of appearance of each variant pattern is similar between the affected individual group and the unaffected individual group, it is possible to determine that there is no significant difference. In other words, it is possible to determine that the variant locus is not correlated with occurrence of the analyzed disease. Meanwhile, for example, as illustrated in FIG. 6 as "example of variant distribution with specificity", at a variant locus where the distribution of the number of times of appearance of each variant pattern is not similar between the affected individual group and the unaffected individual group, there is a significant difference. In other words, it is possible to determine that the variant locus may be correlated with the occurrence of the analyzed disease.

The aggregate result processing device 16 arranges the variant loci in the descending order of the significant difference in the distribution of the number of times of appearance of each variant pattern, and outputs information on a certain number of variant loci in the descending order of the significant difference. An analyst or user analyzes the variant locus correlated with the occurrence of the analyzed disease and the variant patterns at this variant locus, based on the information outputted from the aggregate result processing device 16.

Figure 7:
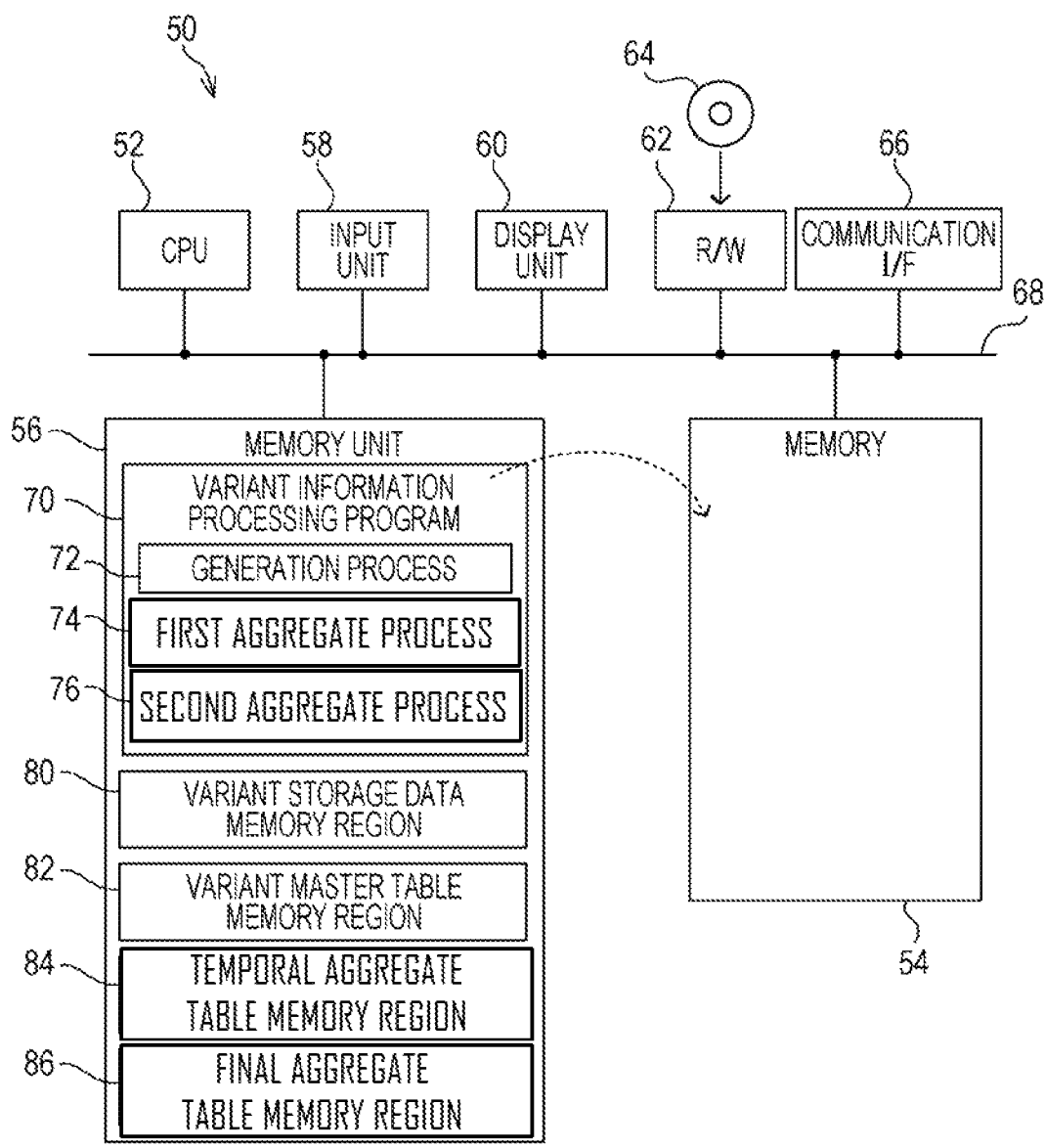
FIG. 7 is a schematic block diagram of a computer which functions as the variant information processing device.

Moreover, in the first embodiment, the variant information processing device 12 is implemented by a computer 50 illustrated in FIG. 7. The computer 50 includes a CPU or processor 52, a memory 54, a non-volatile memory unit 56, an input unit 58, a display 60, a read-and-write device (R/W) 62 which reads and writes data from and to a recording medium 64, and a communication unit 66. The CPU 52, the memory 54, the memory unit 56, the input unit 58, the display unit 60, the R/W 62, and the communication unit 66 are connected to each other by a bus 68. The variant information processing device 12 is capable of communicating with the variant information extraction device 14 and the aggregate result processing device 16 via a network to which the communication unit 66 is connected.

The memory unit 56 is implemented by a hard disk drive (HDD), a solid state drive (SSD), a flash memory, or the like. In the memory unit 56, there are stored a variant information processing program 70 for causing the computer 50 to function as the variant information processing device 12. The CPU 52 reads the variant information processing program 70 from the memory unit 56 to develop the variant information processing program 70 on the memory 54 and sequentially executes processes included in the variant information processing program 70. The variant information processing program 70 includes a generation process 72, a first aggregate processing 74, and a second aggregate processing 76.

The CPU 52 operates as the generator 18 illustrated in FIG. 1 by executing the generation process 72. Moreover, the CPU 52 operates as the first aggregator 20 illustrated in FIG. 1 by executing the first aggregate processing 74. Furthermore, the CPU 52 operates as the second aggregator 22 illustrated in FIG. 1 by executing the second aggregate processing 76. The computer 50 executing the variant information processing program 70 thereby functions as the variant information processing device 12. The variant information processing program 70 is an example of an input support program in the disclosed technique.

Moreover, the memory unit 56 is provided with a variant storage data memory region 80, a variant master table memory region 82, a temporal aggregate table memory region 84, and a final aggregate table memory region 86. The variant storage data 100 is stored in the variant storage data memory region 80 and the variant master table 28 is stored in the variant master table memory region 82. The memory unit 56 thereby functions as the first memory unit 24 illustrated in FIG. 1.

Note that the variant information processing device 12 may be implemented by, for example, a semiconductor integrated circuit, to be more specific, by an application specific integrated circuit (ASIC) or the like.

Next, operations in the first embodiment are described. In the following description, the total number of variant loci is denoted by N and the total number of target individuals to be processed is denoted by M. First, before giving description of a variant storage data generation process executed by the generator 18, a format of the variant storage data generated in this variant storage data generation process is described.

The generator 18 executes the variant storage data generation process to be described later in detail to generate the variant storage data 100 with the format illustrated in FIG. 10, for each individual, by using the variant information (specifically, the VCF file 48 illustrated in FIG. 4) received from the variant information extraction device 14. As illustrated in FIG. 10, the variant storage data 100 includes multiple storage regions 102 each of which has a storage capacity of two bits. An array of the N storage regions 102 (positions 0 to N−1 in the variant storage data 100) from the head of the variant storage data 100 is an array of standard storage regions 102A for storing codes corresponding to the variant patterns at the different variant loci 0 to N−1.

The number s of types of codes storable in the 2-bit storage regions 102 is four $((00)_B, (01)_B, (10)_B,$ and $(11)_B)$. The reason why the storage region 102 is 2 bits is because the number r of types of variant patterns appearing at most (for example, 90% or more) of the N variant loci included in the genetic information is three and it is possible to express the variant patterns by using 2-bit codes when r=3. Note that an example of the variant patterns in the case where the number r of types of variant patterns is three are three patterns of A/A, A/C, and C/C.

The N-th and beyond storage regions 102 (positions=storage regions N and beyond) from the head of the variant storage data 100 are additional storage regions 102B for storing codes corresponding to the variant patterns at the variant loci where the number r of types of variant patterns is greater than four. FIG. 10 illustrates only the additional storage region 102B for the variant locus 2 as the additional storage region 102B. However, the additional storage region 102B is the storage region 102 added for each of the variant loci where the number r of types of variant patterns is greater than four, by the number corresponding the value of the number r of types. At the variant locus where the number r of types of variant patterns is greater than four, codes indicating five or more types of variant patterns may be stored by using one standard storage region 102A and additional storage regions 102B as many as the number corresponding to the value of the number r of types.

Figure 8:
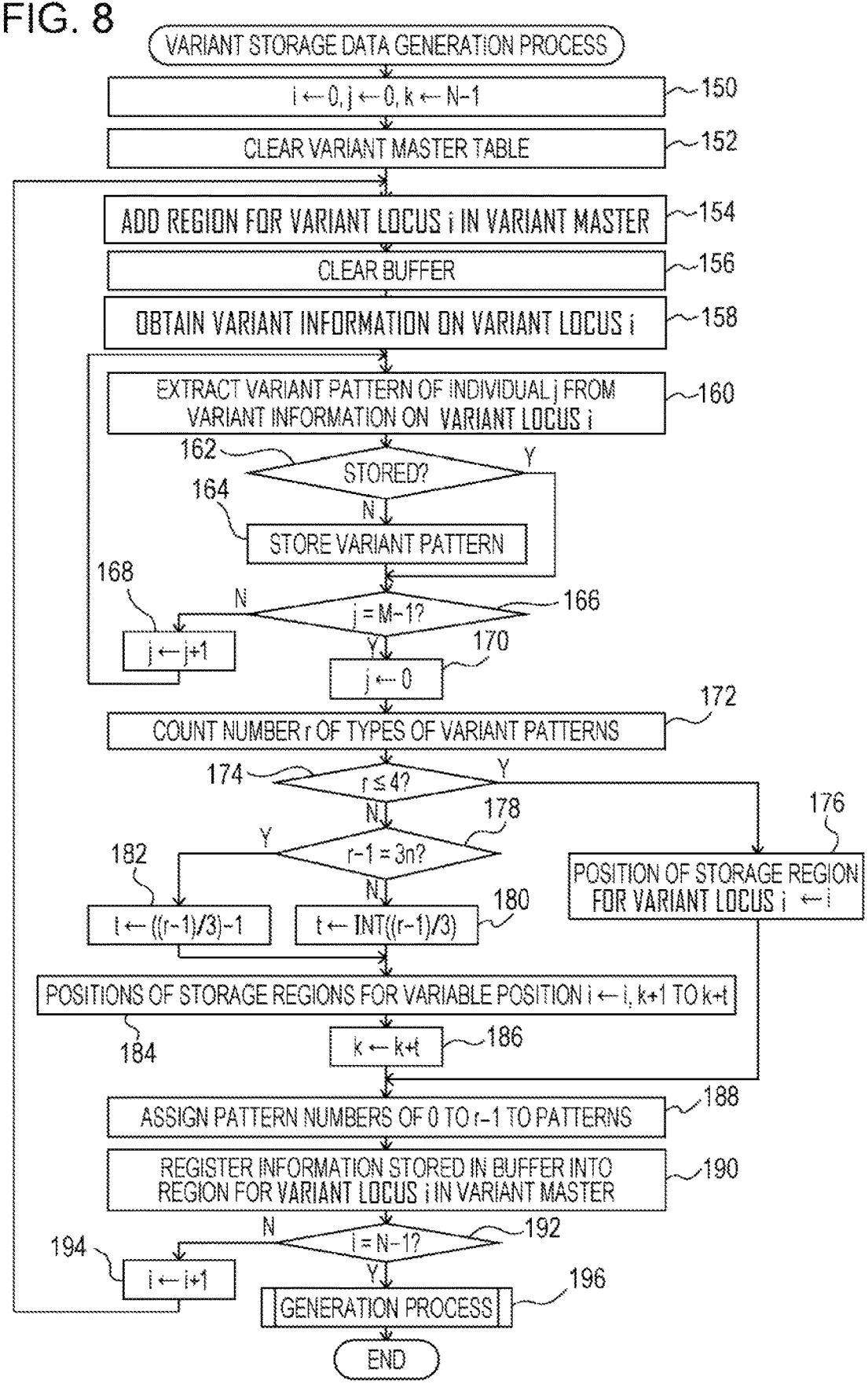
FIG. 8 is a flowchart illustrating a variant storage data generation process.

Next, with reference to FIG. 8, description is given of the variant storage data generation process by which the variant storage data 100 with the aforementioned format is generated. In step 150 of the variant storage data generation process, the generator 18 sets a variable "i" for identifying the variant locus and a variable "j" for identifying the individual to zero, and sets, as initial setting, N−1 to a variable "k" for storing the total number of storage regions 102 included in the variant storage data 100. Moreover, in step 152, the generator 18 clears the variant master table memory region 82 of the memory unit 56 to set the variant master table 28 to an empty state.

In step 154, the generator 18 adds a region for storing information on the variant locus i in the variant master table 28. As illustrated in FIG. 11, in the variant master table 28, there are registered, for each of the variant loci, the positions of all storage regions 102 for the variant locus and information (variant pattern list) indicating a correlation between the variant patterns and the pattern numbers.

In subsequent step 156, the generator 18 clears a buffer region provided in the memory 54 to temporarily store information. In step 158, the generator 18 obtains the variant information 40 at the variant locus i in VCF file 48. For example, when the generator 18 receives the variant information 40 from the variant information extraction device 14 in advance and the received variant information 40 is stored in the memory unit 56, the generator 18 may obtain the variant information 40 on the variant locus i by reading it from the memory unit 56. Meanwhile, the generator 18 may obtain the variant information 40 on the variant locus i by requesting the variant information extraction device 14 to output it, without storing the variant information 40 in the memory unit 56 in advance.

In step 160, the generator 18 extracts the variant pattern at the variant locus i in the individual j, from the variant information on the variant locus i obtained in step 158. In step 162, the generator 18 determines whether the variant pattern at the variant locus i in the individual j extracted in step 160 is stored in the buffer region. In the case where the determination result is no in step 162, the process proceeds to step 164. In step 164, the generator 18 stores the variant pattern at the variant locus i in the individual j extracted in step 160 in the buffer region and the process proceeds to step 166. Meanwhile, when the variant pattern at the variant locus i in the individual j extracted in step 160 is already stored in the buffer region, the determination result is yes in step 162 and the process proceeds to step 166 with step 164 skipped.

In step 166, the generator 18 determines whether the variable j reaches a value obtained by subtracting 1 from the total number M of target individuals to be processed. When the determination result is no in step 166, the process proceeds to step 168. In step 168, the generator 18 increments the variable j by 1 and the process returns to step 160. Steps 160 to 168 are thereby repeated until the determination result of yes is obtained in step 166, and all variant patterns appearing in the individuals being the process targets at the variant locus i are thus stored in the buffer region.

When the determination result is yes in step 166, the process proceeds to step 170. In step 170, the generator 18 sets the variable j to 0. Then, in step 172, the generator 18 counts the number of variant patterns stored in the buffer region to count the number r of types of variant patterns at the variant locus i.

In subsequent step 174, the generator 18 determines whether the number r of types of variant patterns at the variant locus i which is counted in step 172 is four or smaller. When the number r of types of variant patterns at the variant locus i is four or smaller, the variant patterns at the variant locus i is expressible by using 2-bit codes and the additional storage region 102B is unnecessary. Accordingly, when the determination result is yes in step 174, the process proceeds to step 176. In step 176, the generator 18 stores the variable i in the buffer region as the position of the storage region 102 for the variant locus i and the process proceeds to step 188. In this case, for example, as illustrated in FIG. 11 as "variant 0" or "variant 1", only the position ("0" or "1" in the example of FIG. 11) of the standard storage region 102A is stored in the buffer region as the position of the storage region 102.

Meanwhile, when the number r of types of variant patterns at the variant locus i is greater than four, the determination result is no in step 174 and the process proceeds to step 178. When the number r of types of variant patterns at the variant locus i is greater than four, codes for expressing the variant patterns is longer than 2 bits, and the additional storage regions 102B have to be provided. Accordingly, in steps 178 to 182, the number t of additional storage regions which have to be provided is obtained.

Specifically, in step 178, the generator 18 determines whether a value obtained by subtracting 1 from the number r of types of variant patterns at the variant locus i is a multiple of three (see the following formula (1)):

$$r-1=3n \qquad (1)$$ (where $n$ is a natural number).

When the determination result is no in step 178, the process proceeds to step 180. In step 180, the generator 18 calculates the number t of additional storage regions according to the following formula (2) and the process proceeds to step 184:

$$t \leftarrow \text{INT}((r-1)/3) \qquad (2)$$

where INT(a) is the nearest to which a value a is rounded down.

Moreover, when the determination result is yes in step 178, the process proceeds to step 182. In step 182, the generator 18 calculates the number t of the additional storage regions according to the following formula (3) and the process proceeds to step 184:

$$t \leftarrow ((r-1)/3)-1 \qquad (3).$$

In the steps 178 to 182 described above, when the number r of types of variant patterns at the variant locus i is 4<r≤7, the number t of additional storage regions is one. Meanwhile, when the number r is 8<r≤10, the number t of additional storage regions is two. The number t of additional storage regions thus increases by one every time the number r of types increases by three.

In subsequent step 184, the generator 18 stores the variable i and variables k+1 to k+t in the buffer region as the positions of the storage regions 102 for the variable position i. In this case, for example, as illustrated in FIG. 11 as "variant 2", the position of the standard storage region 102A ("2" in the example of FIG. 11) and the position of the additional storage region 102B ("k" in the example of FIG. 11) are stored in the buffer region as the positions of the storage regions 102.

Note that "variant 2" illustrated in FIG. 11 depicts a case where the number t of additional storage regions is one. Since the number t of additional storage regions increases by one every time the number r of types increases by three as described above, the number of positions of the additional storage regions 102B stored in the buffer region also increases by one every time the number r increases by three. In step 186, the generator 18 sets the variable k to a value obtained by adding the number t of additional storage regions to the variable k, and the process proceeds to step 188.

In step 188, the generator 18 assigns different pattern numbers of 0 to r−1 to the respective variant patterns stored in the buffer region, and stores the assigned pattern numbers in the buffer region in association with the variant patterns. In subsequent step 190, the generator 18 registers the information stored in the buffer region as the information on the variant locus i, in the region of the variant master table 28 added in step 154 described above. The information of one row in FIG. 11 are thereby registered in the variant master table 28.

In subsequent step 192, the generator 18 determines whether the variable i reaches a value obtained by subtracting 1 from the total number N of variant loci. When the determination result is no in step 192, the process proceeds to step 194. In step 194, the generator 18 increments the variable i by 1 and the process returns to step 154. Steps 154 to 194 are thereby repeated until the determination result of yes is obtained in step 192, and the positions of the storage regions 102 and the variant pattern lists for all variant loci are registered in the variant master table 28.

When the determination result is yes in step 192, the process proceeds to step 196. In step 196, the generator 18 performs a generation process. The generation process is described below with reference to FIG. 9.

Figure 9:
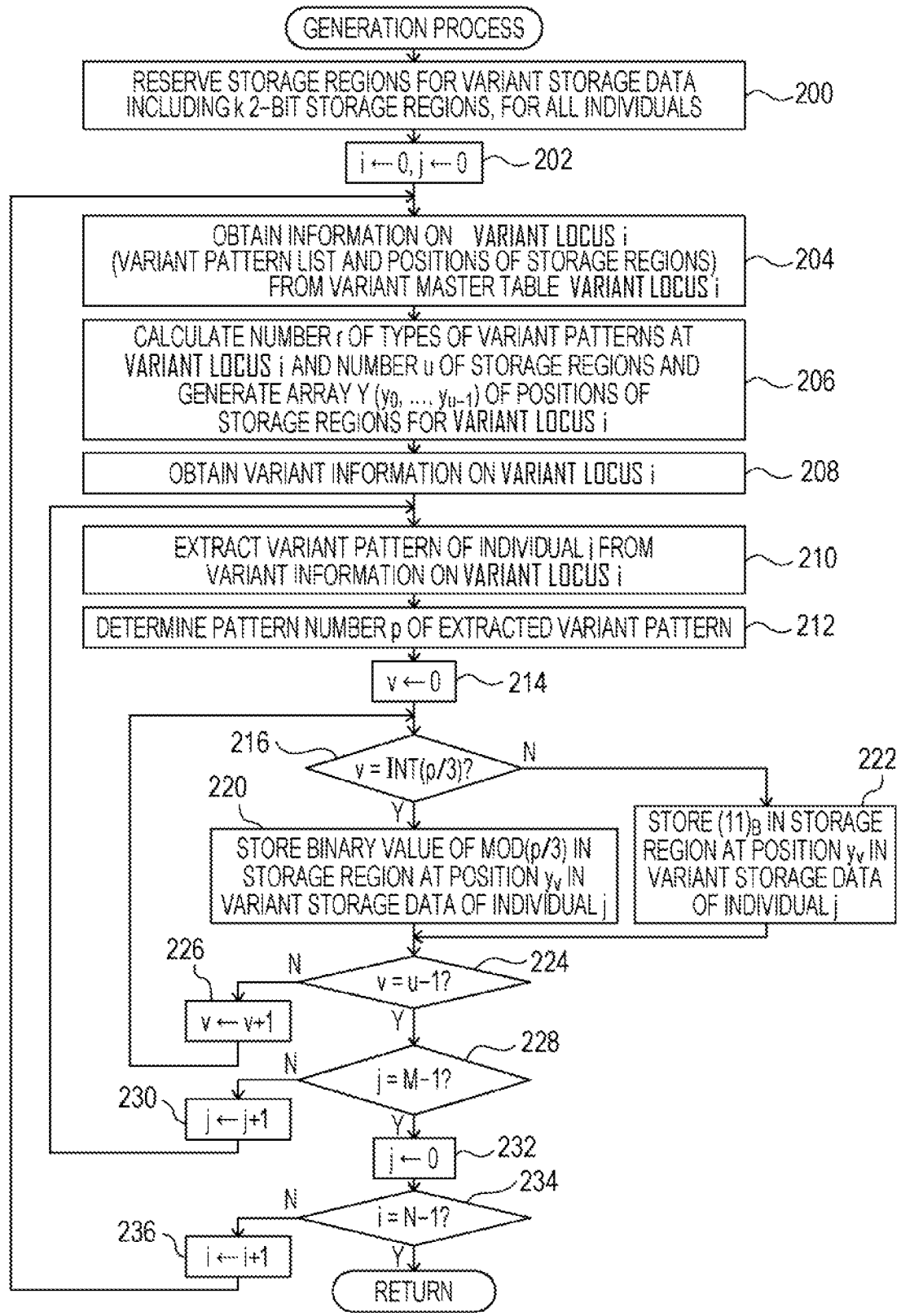
FIG. 9 is a flowchart illustrating a generation process in a first embodiment.

At the time when the generation process illustrated in FIG. 9 is started, the variable k is set to the total number of storage regions 102 assigned to the N variant loci. In step 200, based on this, the generator 18 reserves M storage regions (for all target individuals to be processed) for the variant storage data 100 including k 2-bit storage regions 102, in the variant storage data memory region 80. In subsequent step 202, the generator 18 sets the variable i and the variable j to 0.

In step 204, the generator 18 obtains the information on the variant locus i (positions of the storage regions 102 and the variant pattern list for the variant locus i) from the variant master table 28. In the subsequent step 206, the generator 18 calculates the number r of types of variant patterns at the variant locus i and the number u of storages regions for the variant locus i, based on the information on the variant locus i obtained in step 204. Moreover, the generator 18 generates an array Y ($y_0, \ldots, y_{u-1}$) of the storage region positions in which the positions of the storage regions 102 for the variant locus i are arranged in the ascending order of the positions of the storage regions 102, based on the information on the variant locus i obtained in step 204.

In step 208, the generator 18 obtains the variant information 40 on the variant locus i as in step 158 described above. In step 210, the generator 18 extracts a variant pattern at the variant locus i in the individual j from the variant information 40 on the variant locus i obtained in step 208. In step 212, the generator 18 check the variant pattern extracted in step 210 against the variant pattern list for the variant locus i obtained in step 204 to determine a pattern number p corresponding to the variant pattern at the variant locus i in the individual j.

In step 214, the generator 18 sets a variable v to 0. In step 216, the generator 18 determines whether the variable v matches a value obtained by dividing the pattern number p by 3 and rounding down the divided number to the nearest integer (see the following formula (4)):

$$v=\text{INT}(p/3) \quad (4).$$

When the determination result is yes in step 216, the process proceeds to step 220. In step 220, the generator 18 stores a binary value indicating the remainder of the pattern number p divided by 3, in the storage region 102 at a position yv in the variant storage data 100 of the individual j (see the following formula (5):

$$\text{Pattern } [j][yv] \leftarrow \text{MOD}(p/3) \quad (5)$$

where Pattern [j][yv] represents the storage region 102 at the position yv in the variant storage data 100 of the individual j, and MOD(a/b) represents a remainder of a/b.

Meanwhile, when the determination result is no in step 216, the process proceeds to step 222. In step 222, the generator 18 stores a code $(11)_B$ in the storage region 102 at the position yv in the variant storage data 100 of the individual j. Note that $(11)_B$ is an example of a specific code. After step 220 or 222 is performed, the process proceeds to step 224.

In step 224, the generator 18 determines whether the variable v reaches a value obtained by subtracting 1 from the number u of the storage regions for the variant locus i. When the determination result is no in step 224, the process proceeds to step 226. In step 226, the generator 18 increments the variable v by 1 and the process returns to step 216. Steps 216 to 226 are thereby repeated until the determination result of yes is obtained in step 224, and the code corresponding to the pattern number p is stored in each of the storage regions 102 for the variant locus i in the variant storage data 100 of the individual j. Then, when the determination result of yes is obtained in step 224, the process proceeds to step 228.

In step 228, the generator 18 determines whether the variable j reaches the value obtained by subtracting 1 from the total number M of the target individuals to be processed. When the determination result is no in step 228, the process proceeds to step 230. In step 230, the generator 18 increments the variable j by 1 and the process returns to step 210. Steps 210 to 230 are thereby repeated until the determination result of yes is obtained in step 228. Accordingly, the process of sequentially extracting the variant patterns at the variant locus i in the individuals from the variant information 40 obtained in step 208 and storing the codes corresponding to the extracted variant patterns in the storage regions 102 for the variant locus i in the variant storage data 100 of the individuals is repeated.

When the determination result is yes in step 228, the process proceeds to step 232. In step 232, the generator 18 sets the variable j to 0. In subsequent step 234, the generator 18 determines whether the variable i reaches the value obtained by subtracting 1 from the total number N of variant loci. When the determination result is no in step 234, the process proceeds to step 236. In step 236, the generator 18 increments the variable i by 1 and the process returns to step 204. Steps 204 to 236 are thereby repeated until the determination result of yes is obtained in step 234, and the codes are stored in the variant storage data 100 of the individuals for all variant loci. Then, when the determination result is yes in step 234, the generation process as the variant data storage process illustrated in FIG. 8 is terminated.

FIGS. 13 and 14 illustrate an example of codes stored in the storage regions 102 for one variant locus in the variant storage data 100, as an example of the process result of the aforementioned generation process illustrated in FIG. 9. FIGS. 13 and 14 illustrate relationships between the pattern numbers p (=0 to 9) and the binary values stored in the storage regions 102 when the number u of storage regions for a same variant locus is three and the number r of types of variant patterns at this variant locus is ten. Note that "NULL" in FIG. 13 and the like is the code $(11)_B$ in this specification.

For example, when three 2-bit storage regions 102 are allocated for one variant locus, the number s of types of codes storable in the three storage regions 102 is $s=2^6=64$, assuming that the storage regions 102 are integral (6-bit storage region), and it is possible to express 64 types of variant patterns. As an specific example of this case, FIG. 12 illustrates an example in which a code $(001101)_B$ is stored in the three storage regions 102 assumed to be integral. However, there are 64/4=16 types of variant patterns which may be expressed by a code of a certain value stored in one storage region 102, and it is impossible to determine the variant pattern expressed by the codes in the three storage regions 102 from the code of the certain value stored in the one storage region 102. Accordingly, in the aggregate processing, a process of obtaining the codes from the three storage regions, checking the obtained three codes against similar information in the variant master table 28 to determine the variant pattern, and incrementing an aggregate value of the determined variant pattern has to be performed.

Meanwhile, in the embodiment, a code corresponding to a variant pattern is stored in one storage region 102 as a specific storage region for the variant pattern such as the pattern number p among the storage regions 102 for the single variant locus, and the code $(11)_B$ is stored in the rest of the storage regions 102. For example, in the example of FIGS. 13 and 14, when the pattern number p is 0 to 2, "region 0" is used as the specific storage region and a code (one of $(00)_B$ to $(10)_B$) corresponding to the pattern number p is stored in "region 0" while the code $(11)_B$ is stored in "region 1" and "region 2". Meanwhile, when the pattern number p is 3 to 5, "region 1" is used as the specific storage region and a code (one of $(00)_B$ to $(10)_B$) corresponding to the pattern number p is stored in "region 1" while the code $(11)_B$ is stored in "region 0" and "region 2". Moreover, when the pattern number p is 6 to 8, "region 2" is used as the specific storage region and a code (one of $(00)_B$ to $(10)_B$) corresponding to the pattern number p is stored in "region 2" while the code $(11)_B$ is stored in "region 0" and "region 1". Then, when the pattern number p is 9, the code $(11)_B$ is exceptionally stored in "region 0" to "region 2".

In the example of FIGS. 13 and 14, the number of types of variant patterns expressible by three storage regions 102 is ten. However, in the example of FIGS. 13 and 14, each of the codes ($(00)_B$ to $(10)_B$) stored in the storage regions 102 and corresponding to the pattern numbers p corresponds to one variant pattern (pattern number p). Moreover, in the example of FIGS. 13 and 14, $(11)_B$ stored in the storage regions other than the specific storage regions represents that no code corresponding to the pattern number p is stored in these regions, except for the case where the pattern number p is 9.

Accordingly, in the aggregate processing to be described later, it is possible to first perform a temporal aggregate processing of aggregating how many times each of the codes stored in each of the storage regions 102 in the variant storage data 100 appears with respect to each of the storage regions 102 and each of codes in all target individuals to be processed. The temporal aggregate processing is a process which is repeated as many times as the product of the total number M of the target individuals to be processed and the number k of storage regions. However, since the variant information processing device 12 does not have to refer to the variant master table 28 in the temporal aggregate processing, it is possible to perform the temporal aggregate processing at high speed. Then, after the temporal aggregate processing, it is possible to perform a final aggregate processing of aggregating how many times each of types of variant patterns in all target individuals to be processed appears at each of the variant loci, from the aggregate result of the temporal aggregate processing.

Note that the example illustrated in FIGS. 13 and 14 is the example in which the number u of storage regions is three and the number r of types of variant patterns is ten. When the number r of types is not 3n+1, there is no pattern number p for which the code $(11)_B$ is stored in all storage regions 102 for the single variant locus. Moreover, when the number r of types is equal to or smaller than four, the number u of storage region is one, and one storage region 102 for the variant locus, that is, the standard storage region 102A is used as the specific storage region to store the code (one of $(00)_B$ to $(10)_B$) corresponding to the pattern number p.

Figure 17:
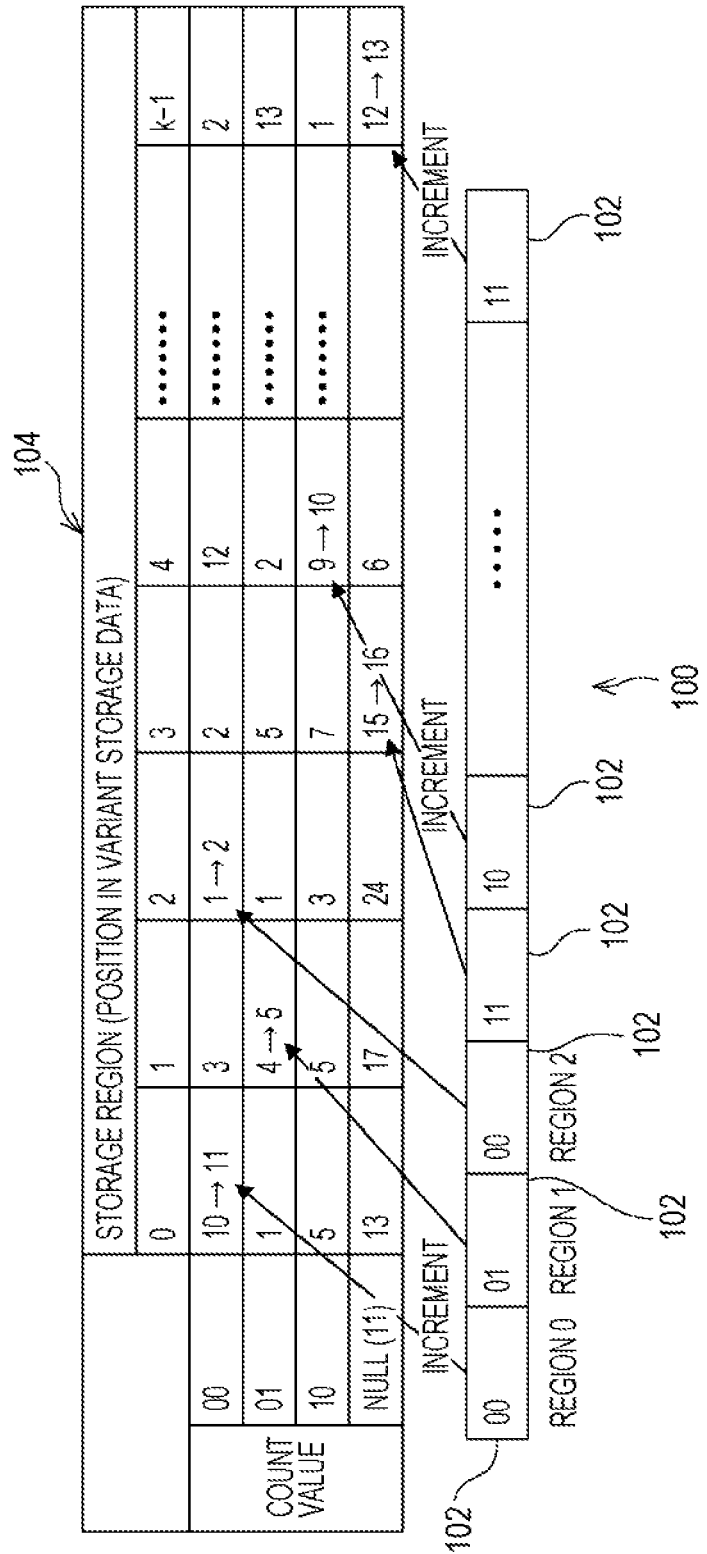
FIG. 17 is a conceptual diagram illustrating an outline of temporal aggregating using a temporal aggregate table.

Next, the aggregate processing executed after the termination of the aforementioned variant data storage process is described with reference to FIG. 15. A temporal aggregate table 104 an example of which is illustrated in FIG. 17 is stored in the temporal aggregate table memory region 84 of the memory unit 56. The temporal aggregate table 104 stores an aggregate value of each code (each of $(00)_B$ to $(11)_B$) in each storage region in the variant storage data 100.

In step 250 of the aggregate processing, the first aggregator 20 sets all aggregate values stored in the temporal aggregate table 104 to zero, as a result, the temporal aggregate table 104 is initialized. In the following description, the aggregate value of a code x in the storage region 102 at a position w which is stored in the temporal aggregate table 104 is expressed as TempAgg[w][x].

In step 252, the first aggregator 20 sets the variable j and a variable w for identifying the position of each storage region 102 to zero. In step 254, the first aggregator 20 obtains the variant storage data 100 of the individual j from the variant storage data memory region 80 of the memory unit 56. In step 256, the first aggregator 20 extracts a code x stored in the storage region 102 at the position w, from the variant storage data 100 of the individual j obtained in step 254.

In subsequent step 258, the first aggregator 20 increments the aggregate value TempAgg[w][x] of the code x in the storage region at the position w among the aggregate values stored in the temporal aggregate table 104 by 1. In step 260, the first aggregator 20 determines whether the variable w reaches a value obtained by subtracting 1 from the number k of storage regions. When the determination result is no in step 260, the process proceeds to step 262. In step 262, the first aggregator 20 increments the variable w by 1 and the process returns to step 256. Steps 254 to 262 are thereby repeated until the determination result of yes is obtained in step 260 and, as illustrated in FIG. 17 as an example, how many times each code appears in each storage regions and each of codes is aggregated according to the codes stored in the storage regions of the variant storage data 100 of the individual j.

When the determination result is yes in step 260, the process proceeds to step 264. In step 264, the first aggregator 20 sets the variable w to zero. In subsequent step 266, the first aggregator 20 determines whether the variable j reaches the value obtained by subtracting 1 from the total number M of the target individuals to be processed. When the determination result is no in step 266, the process proceeds to step 268. In step 268, the first aggregator 20 increments the variable j by 1 and the process returns to step 254.

Steps 254 to 268 are thereby repeated until the determination result of yes is obtained in step 266. Accordingly, there is performed the temporal aggregate processing of sequentially obtaining pieces of the variant storage data 100 of the respective individuals and aggregating how many times each code appears in each storage region, according to the codes stored in the storage regions of the obtained variant storage data 100. Since the aggregating is performed without referring to the variant master table 28 in the temporal aggregate processing described above, the speed of process is increased.

Figure 16:
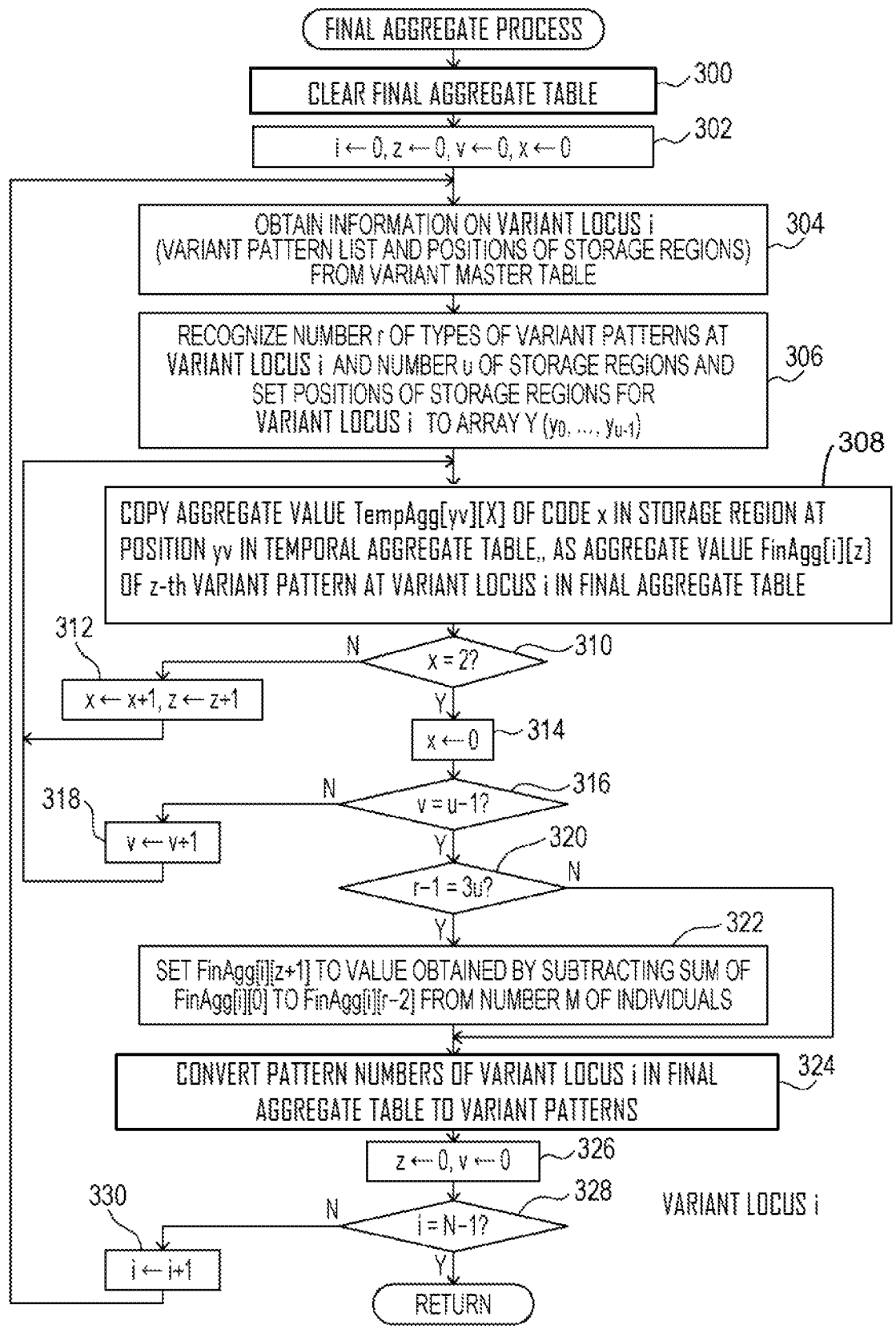
FIG. 16 is a flowchart illustrating a final aggregate processing in the first embodiment.
Figure 18:
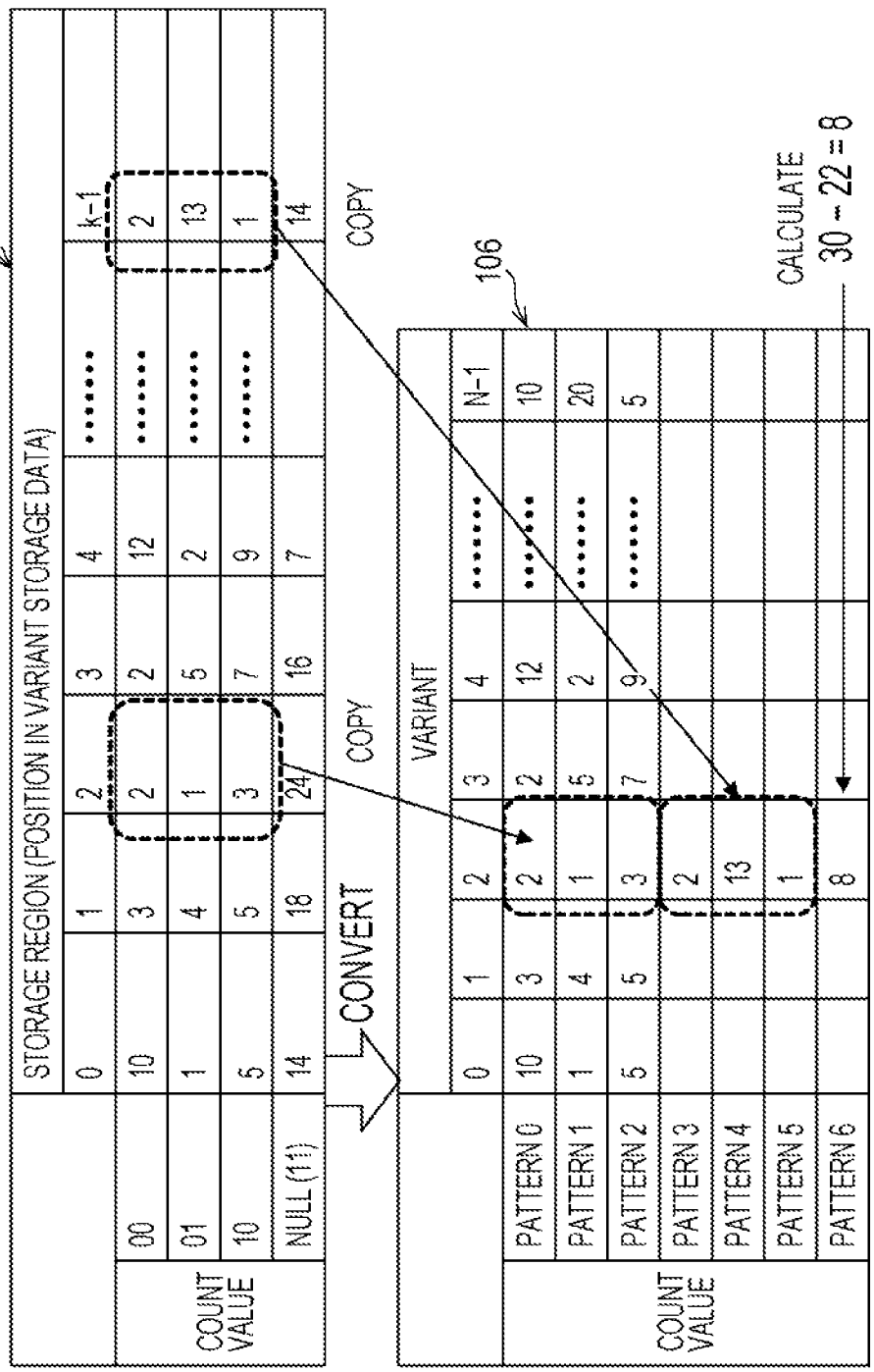
FIG. 18 is a conceptual diagram illustrating an outline of final aggregating using a final aggregate table in the first embodiment.

When the determination result is yes in step 266, the process proceeds to step 270. In step 270, the second aggregator 22 performs the final aggregate processing. The final aggregate processing is described below with reference to FIG. 16. A final aggregate table 106 an example of which is illustrated in FIG. 18 is stored in the final aggregate table memory region 86 of the memory unit 56. The final aggregate table 106 is provided with storage regions for storing the aggregate value of each pattern number p (each variant pattern) at each variant locus.

In the step 300 of the final aggregate processing, the second aggregator 22 sets all aggregate values stored in the final aggregate table 106, as a result, the final aggregate table 106 is initialized. In the following description, the aggregate value of the z-th variant pattern at the variant locus i which is stored in the final aggregate table 106 is expressed as FinAgg[i][z].

In step 302, the second aggregator 22 sets the variable i, a variable z for identifying the variant pattern (pattern number p), the variable v, and the variable x to zero. Then, in step 304, the second aggregator 22 obtains the information on the variant locus i (positions of the storage regions 102 and the variant pattern list for the variant locus i) from the variant master table 28.

In step 306, the second aggregator 22 calculates the number r of types of variant patterns at the variant locus i and the number u of storage regions for the variant locus i, based on the information on the variant locus i obtained in step 204. Moreover, the second aggregator 22 generates an array Y ($y_0, \ldots, y_{u-1}$) of the storage region positions in which the positions of the storage regions 102 for the variant locus i are arranged in the ascending order of the positions of the storage regions 102, based on the information on the variant locus i obtained in step 304.

In step 308, the second aggregator 22 copies the aggregate value TempAgg[yv][x] of the code x in the storage region at the position yv in the temporal aggregate table 104, into a memory region for the aggregate value FinAgg[i][z] of the z-th variant pattern at the variant locus i in the final aggregate table 106. In step 310, the second aggregator 22 determines whether the value of the variable x reaches 2. When the determination result is no in step 310, the process proceeds to step 312. In step 312, the second aggregator 22 increments the variable x by 1 and also increments the variable z by 1 and the process returns to step 308. Steps 308 to 312 are thereby repeated until the determination result of yes is obtained in step 310.

Meanwhile, when the determination result is yes in step 310, the process proceeds to step 314. In step 314, the second aggregator 22 sets the variable x to zero. In subsequent step 316, the second aggregator 22 determines whether the variable v reaches the value obtained by subtracting 1 from the number u of storage regions for the variant locus i. When the determination result is no in step 316, the process proceeds to step 318. In step 318, the second aggregator 22 increments the variable v by 1 and the process returns to step 308. Steps 308 to 318 are thereby repeated until the determination result of yes is obtained in step 316.

In steps 308 to 318 described above, a group of aggregate values in the storage regions for each of the variant loci i which are stored in the temporal aggregate table 104 are copied into a group of memory regions for the aggregate values at the variant locus i in the final aggregate table 106. As an example, FIG. 18 illustrates an example in which a group of aggregate values in the storage regions at the positions 2 and k−1 for the variant locus 2 which are stored in the temporal aggregate table 104 are copied into a group of memory regions for the aggregate values at the variant locus 2 in the final aggregate table 106, as denoted by "copy".

Meanwhile, when the determination result is yes in step 316, the process proceeds to step 320. In step 320, the second aggregator 22 determines whether the value obtained by subtracting 1 from the number r of types of variant patterns matches a value obtained by multiplying the number u of the storage regions by 3 (see the following formula (6)):

$$r-1=3u \qquad (6).$$

When the determination result is no in step 320, the final variant pattern (variant pattern with the pattern number p=r−1) among r types of variant patterns at the variant locus i is a variant pattern for which the code $(11)_B$ is stored in all storage regions 102 for the variant locus i. An example of such a variant pattern is the variant pattern corresponding to the pattern number p=9 in the example illustrated in FIG. 14. When the determination result is yes in step 320, the process proceeds to step 322.

For example, in the example illustrated in FIG. 14, the code $(11)_B$ is stored in the storage region 0 when the pattern number p is 3 to 9, in the storage region 1 when the pattern number p is 0 to 2 and 6 to 9, and in the storage region 2 when the pattern number p is 0 to 5. Accordingly, the aggregate value of the final variant pattern at the variant locus i has to be obtained by calculation.

In step 322, the second aggregator 22 sets the aggregate value FinAgg[i][z+1] of the (z+1)th variant pattern at the variant locus i in the final aggregate table 106 to a value obtained by subtracting the sum of the aggregate values FinAgg[i][0] to FinAgg[i][r−1] from the total number M of individuals. Note that the total number M of individuals is equal to the sum of the aggregate values TempAgg[yv][0] to TempAgg[yv][3] of codes x=$(00)_B$ to $(11)_B$ in the storage region at the position yv (variable v is any one of 0 to u−1) for the variable position i which are stored in the temporal aggregate table 104. Accordingly, the process of step 322 is expressible by the following formula (6) or (7).

$$FinAgg[i][z+1] \leftarrow M - \sum_{z=0}^{r-1} FinAgg[1][z] \qquad (6)$$

$$FinAgg[i][z+1] \leftarrow \sum_{x=0}^{3} TempAgg[yv][x] - \sum_{z=0}^{r-1} FinAgg[i][z] \qquad (7)$$

For example, in FIG. 18, as denoted by "calculation", the sum (=22) of the aggregate values of the variant patterns with the pattern numbers p=0 to 5, that is, variant patterns other than the final variant pattern (pattern number p=6) is subtracted from the total number M (=30) of individuals to calculate the aggregate value of the final variant pattern.

Meanwhile, when the determination result is no in step 320, there is no variant pattern to which a code of storing the code $(11)_B$ in all storage regions 102 for the variant locus i is assigned, among the r types of variant patterns appearing at the variant locus i. Accordingly, when the determination result is no in step 320, step 322 is skipped and the process proceeds to step 324. In the process described above, how many times each variant pattern (pattern number p) appears at the variant locus i is stored in the final aggregate table 106.

In step 324, the second aggregator 22 converts the pattern numbers at the variant locus i stored in the final aggregate table to the corresponding variant patterns, based on the variant pattern list of the variant locus i obtained from the variant master table 28. In subsequent step 326, the second aggregator 22 sets the variables z and v to zero.

In subsequent step 328, the second aggregator 22 determines whether the variable i reaches the value obtained by subtracting 1 from the total number N of variant loci. When the determination result is no in step 328, the process proceeds to step 330. In step 330, the second aggregator 22 increments the variable i by 1 and the process returns to step 304. Steps 304 to 330 are thereby repeated until the determination result of yes is obtained in step 328. The aforementioned final aggregate processing is performed for all variant loci.

The final aggregate processing described above includes a process of accessing the variant master table 28. However, since the aggregating in units of storage regions 102 for all target individuals to be processed is already completed in the temporal aggregate processing (steps 250 to 268 in FIG. 15) described above, the number of times the process is repeated in the final aggregate processing is N (the number of variant loci). Accordingly, an effect of including the process of accessing the variant master table 28 on the process time is far smaller than that in the temporal aggregate processing in which the process would otherwise be repeated M (total number of target individuals to be processed)×k (the number of storage regions) times.

Figure 15:
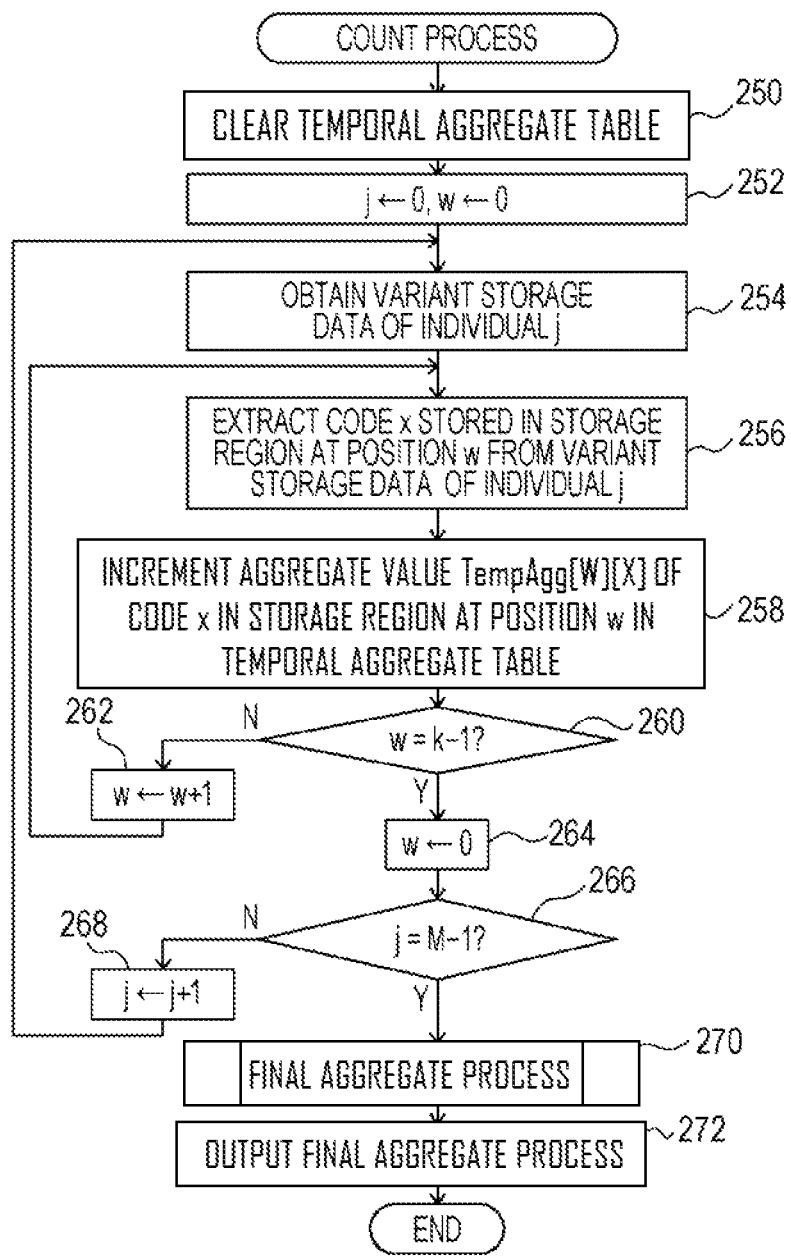
FIG. 15 is a flowchart illustrating an aggregate processing.

When the determination result is yes in step 328, the final aggregate processing is terminated and the process proceeds to step 272 of the aggregate processing (FIG. 15). In step 272, the second aggregator 22 outputs the final aggregate result (result of aggregating how many times the variant pattern for each of the types of variant patterns in all target individuals to be processed appears at each of the variant loci) obtained in the aforementioned process, to the aggregate result processing device 16 and the aggregate processing is terminated.

Embodiment 2

Next, a second embodiment of the disclosed technique is described. Since a configuration of the second embodiment is same as that of the first embodiment, description of the configuration is omitted by denoting parts with the same reference numerals. Operations in the second embodiment which are different from those in the first embodiment are described below.

Figure 19:
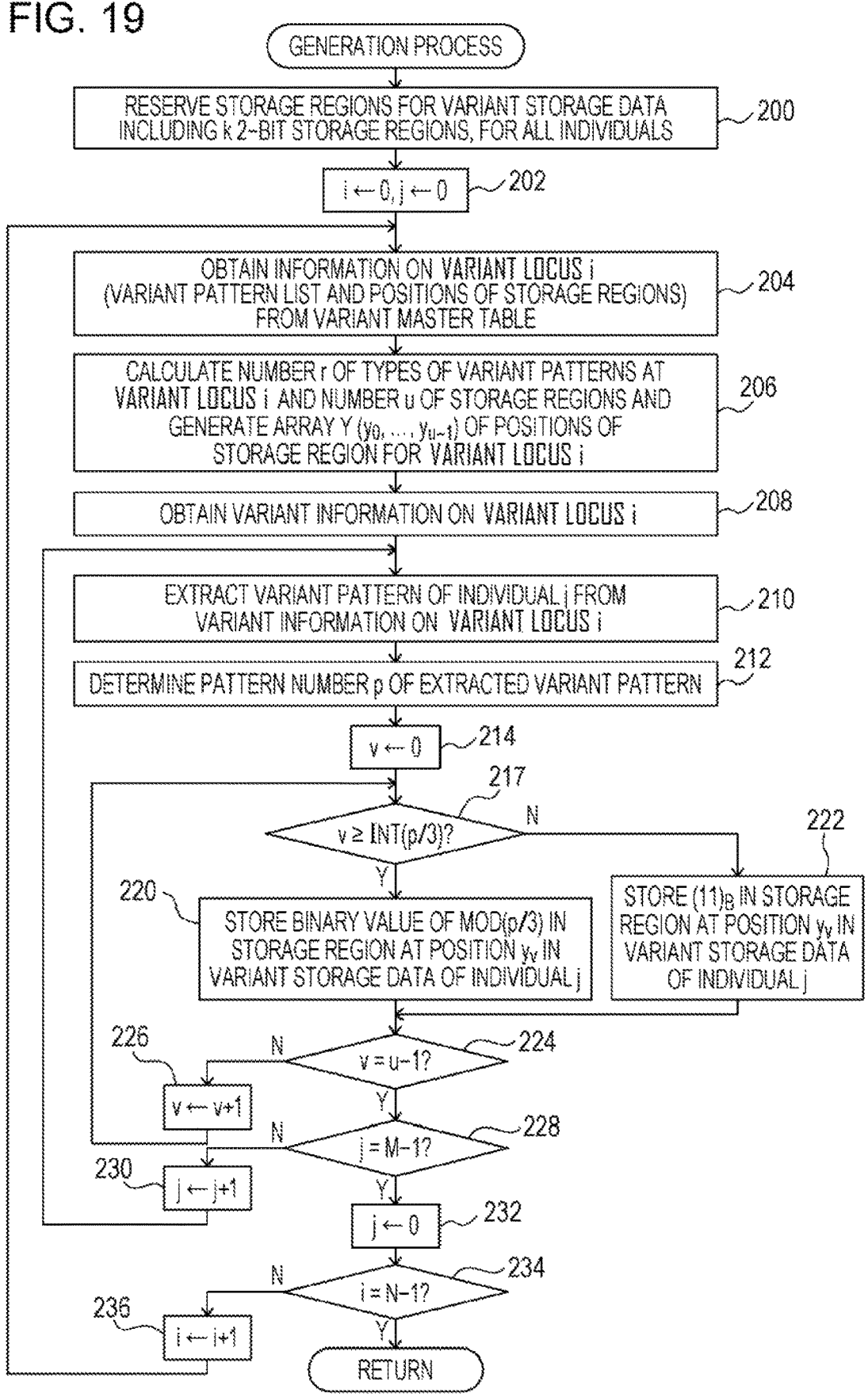
FIG. 19 is a flowchart illustrating a generation process in a second embodiment.

First, a generation process in the second embodiment is described with reference to FIG. 19. The generation process in the second embodiment is different from the generation process illustrated in FIG. 9 and described in the first embodiment in that determination of step 217 is performed instead of step 216. In step 217, the generator 18 determines whether the variable v is equal to or greater than a value obtained by dividing the pattern number p by 3. When the determination result is yes in step 217, the process proceeds to step 220. When the determination result is no in step 217, the process proceeds to step 222.

FIGS. 20 and 21 illustrate an example of codes stored in the storage regions 102 for one variant locus in the variant storage data 100, as an example of a process result of the generation process in the second embodiment. FIGS. 20 and 21 illustrate relationships between the pattern numbers p (=0 to 9) and the binary values stored in the storage regions 102 when the number u of storage regions for a single variant locus is three and the number r of types of variant patterns at the variant locus is ten.

In the second embodiment, a code corresponding to a variant pattern is stored in one storage region 102 (specific storage region) corresponding to the variant pattern (pattern number p) among the storage regions 102 for the single variant locus. Moreover, the same code as that in the specific storage region is stored in the rest of the storage regions 102 for the variant locus in front of which the specific storage region exists in the variant storage data 100 (first storage region(s) 102). Furthermore, $(11)_B$ is stored in the rest of the storage regions 102 for the variant locus behind which the specific storage region exists in the variant storage data 100 (second storage region(s) 102).

For example, in the example of FIGS. 20 and 21, when the pattern number p=0 to 2, "region 0" is used as the specific storage region to store the code (one of $(00)_B$ to $(10)_B$) corresponding to the pattern number p, and the same code as that in the specific storage region is stored also in "region 1" and "region 2". Meanwhile, when the pattern number p=3 to 5, "region 1" is used as the specific storage region to store the code (one of $(00)_B$ to $(10)_B$) corresponding to the pattern number p, the code $(11)_B$ is stored in "region 0", and the same code as that in the specific storage region is stored in "region 2". Moreover, when the pattern number p=6 to 8, "region 2" is used as the specific storage region to store the code (one of $(00)_B$ to $(10)_B$) corresponding to the pattern number p, and the code $(11)_B$ is stored in "region 0" and "region 1". Then, when the pattern number p is 9, the code $(11)_B$ is exceptionally stored in "region 0" to "region 2".

In the example of FIGS. 20 and 21, the code (one of $(00)_B$ to $(10)_B$) corresponding to the pattern number p and stored in each set of the three storage regions 102 corresponds to one variant pattern (pattern number p). Moreover, in the example of FIGS. 20 and 21, $(11)_B$ stored in the storage region(s) other than the specific storage region except for the case where the pattern number p=9 represents that no code corresponding to the pattern number p is stored in the region(s).

Accordingly, as in the first embodiment, in the aggregate processing, it is possible to first perform the temporal aggregate processing of aggregating how many times each of the codes stored in each of the storage regions 102 in the variant storage data 100 appears in all target individuals to be processed appears. The temporal aggregate processing is a repeated process which is repeated as many times as the product of the total number M of the target individuals to be processed and the number k of storage regions. However, since the variant information processing device 12 does not have to refer to the variant master table 28 in the temporal aggregate processing, it is possible to perform the temporal aggregate processing at high speed. Then, after the temporal aggregate processing, it is possible to perform the final aggregate processing of aggregating how many times each of types of variant patterns in all target individuals to be processed appears at each of the variant loci, from the aggregate result of the temporal aggregate processing.

Note that the example illustrated in FIGS. 20 and 21 is the example in which the number u of storage regions is three and the number r of types of variant patterns is ten. When the number r of types is not 3n+1, there is no pattern number p for which the code $(11)_B$ is stored in all storage regions 102 for the single variant locus. Moreover, when the number r of types is equal to or smaller than four, the number u of storage region is one, and one storage region 102 for the variant locus, that is, the standard storage region 102A is used as the specific storage region to store the code (one of $(00)_B$ to $(10)_B$) corresponding to the pattern number p.

Figure 22:
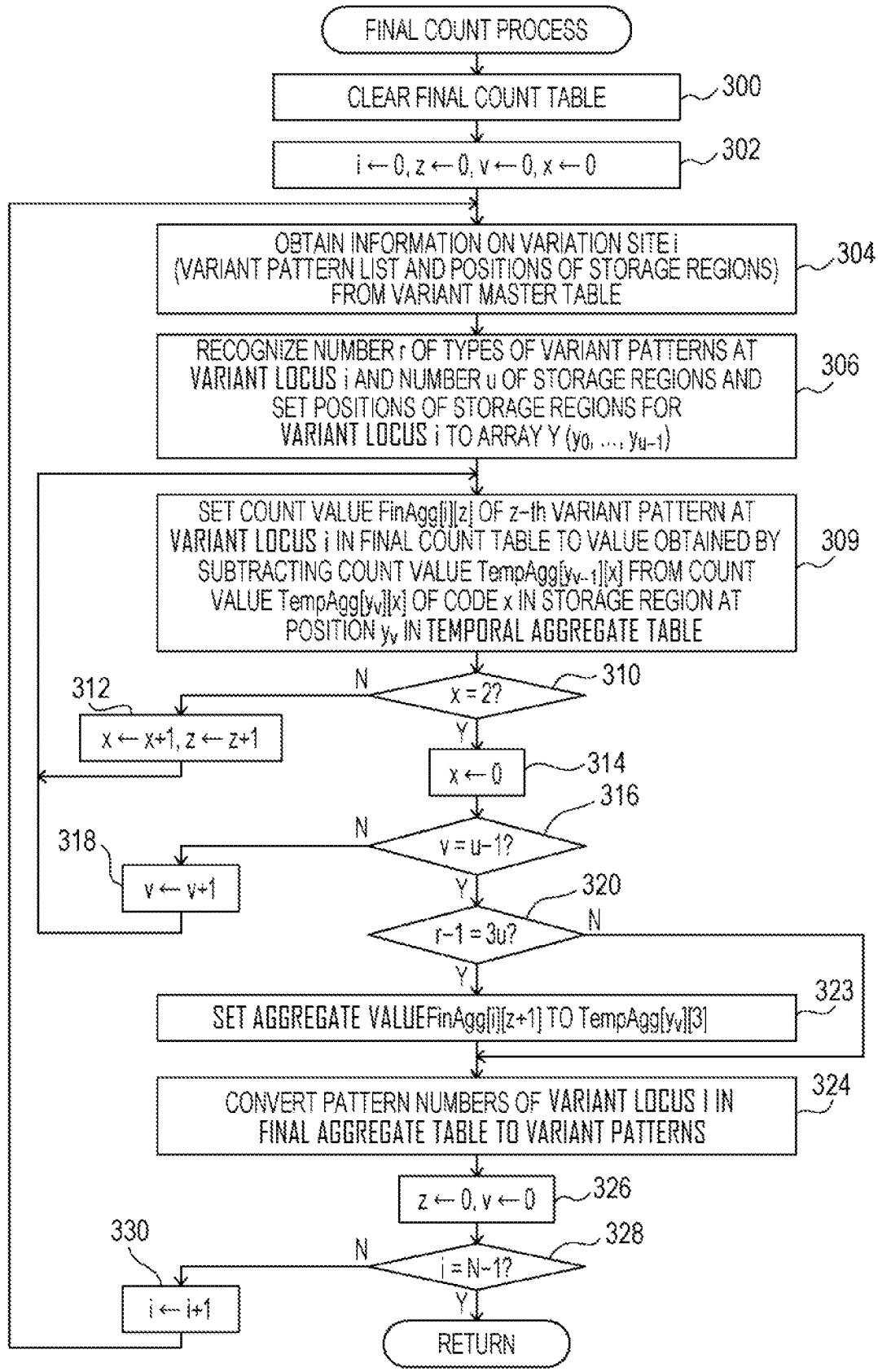
FIG. 22 is a flowchart illustrating a final aggregate processing in the second embodiment.

Next, a final aggregate processing in the second embodiment is described with reference to FIG. 22. The final aggregate processing in the second embodiment is different from the final aggregate processing illustrated in FIG. 16 and described in the first embodiment in that determination of step 309 is performed instead of step 308. In step 309, the second aggregator 22 calculates a value obtained by subtracting an aggregate value $TempAgg[y_{v-1}][x]$ from an aggregate value $TempAgg[y_v][x]$ of the code x in the storage region 102 at the position $y_v$ in the temporal aggregate table 104. Then, the second aggregator 22 sets the calculated value to an aggregate value $FinAgg[i][z]$ of the z-th variant pattern at the variant locus i in the final aggregate table 106. However, when v=0 (v−1=−1), $TempAgg[y_{v-1}][x]$ is zero.

Figure 23:
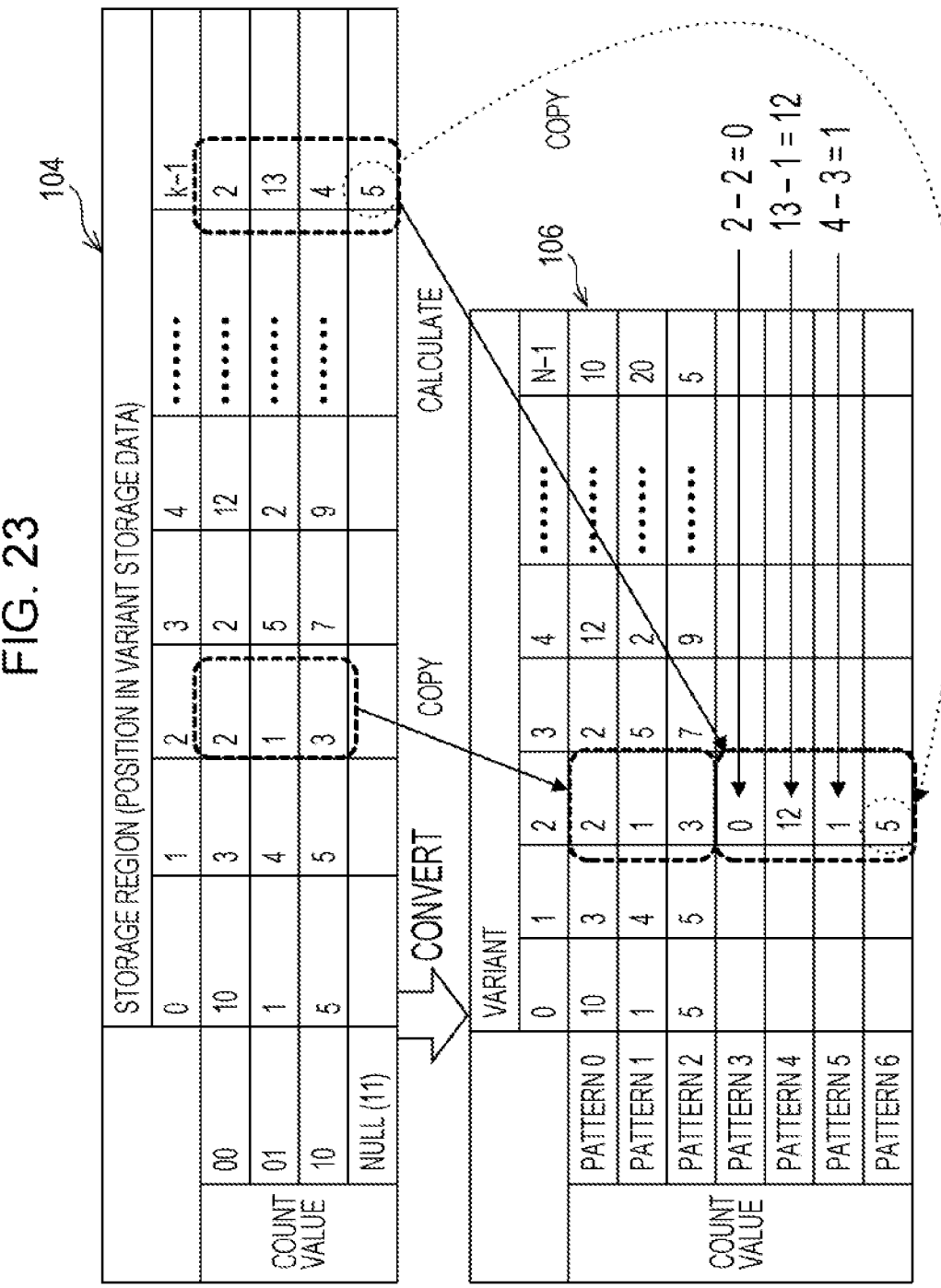
FIG. 23 is a conceptual diagram illustrating an outline of final aggregating using a final aggregate table in the second embodiment.

In steps 308 to 318 including step 309 described above, the aggregate values in the first storage region for each of the variant loci i in the temporal aggregate table 104 are copied into the memory regions for the aggregate values at the variant locus i in the final aggregate table 106. For example, FIG. 23 illustrates an example in which the aggregate values in the storage region at the position 2 corresponding to the variant locus 2 in the temporal aggregate table 104 are copied into memory regions for the aggregate values of the patterns 0 to 2 at the variant locus 2 in the final aggregate table 106, as denoted by "copy".

Moreover, for each of the variant loci, the aggregate values in the second and beyond storage regions for each of the variant loci i in the temporal aggregate table 104 are reduced by the aggregate values in one previous storage regions for the same variant locus and the resultant values are set in the memory regions for the aggregate values at the variant locus i in the final aggregate table 106. In the example illustrated in FIG. 23, the aggregate values of the codes $(00)_B$ to $(10)_B$ in the storage region at the position k−1 for the variant locus 2 in the temporal aggregate table 104 are reduced by the aggregate values in the storage region at the position 2 which is one previous storage region for the same variant locus. Then, the reduced values are set in the memory regions for the aggregate values of the patterns 3 to 5 at the variant locus 2 in the final aggregate table 106.

Moreover, the final aggregate processing in the second embodiment is different from the final aggregate processing described in the first embodiment in that a process of step 323 is performed instead of step 322. In step 323, the second aggregator 22 sets the aggregate value FinAgg[i][z+1] of the pattern number p=(z+1) at the variant locus i in the final aggregate table 106 to an aggregate value TempAgg[$y_v$][3] of a code 3 ($=(11)_B$) at the position $y_v$ in the temporal aggregate table 104. In the example illustrated in FIG. 23, an aggregate value of the code $(11)_B$ in the storage region at the position k−1 for the variant locus 2 in the temporal aggregate table 104 is copied into a memory region for the aggregate value of the pattern 6 at the variant locus 2 in the final aggregate table 106, as denoted by "copy".

Also in the final aggregate processing in the second embodiment which includes steps 309 and 323 described above, how many times each variant pattern (pattern number p) appears at each variant locus is stored in the final aggregate table 106.

As described above, in the aforementioned embodiments, the generator 18 generates the variant storage data 100 of each of multiple target individuals to be processed, from the variant information 40 including information indicating the variant patterns of each of the individuals to be processed at each of the variant loci in the genetic information. The generation of the variant storage data 100 is performed while switching the process as follows depending on whether each of the variant loci is the first variant locus or the second variant locus, the first variant locus being the site where the number r of types of variant patterns in the multiple target individuals to be processed is equal to or smaller than four, the second variant locus being the site where the number r of types is greater than four. Specifically, for the first variant locus, the code corresponding to the variant pattern at the first variant locus is stored in the standard storage region 102A for the first variant locus in the array of standard storage regions 102A for the variant loci. For the second variant locus, the group of the standard storage region 102A for the second variant locus and the additional storage regions 102B for the second variant locus added behind the array of the standard storage regions 102A are divided into a specific storage region for the variant pattern at the second variant locus and the rest of the storage regions. Then, the code corresponding to the variant pattern at the second variant locus is stored in the specific storage region and the certain code is stored in the rest of the storage regions.

Hence, it may be possible to increase the speed of the aggregate processing of aggregating how many times each variant pattern appears at each variant locus in the genetic information.

Moreover, in the embodiments described above, the generator 18 extracts all types of variant patterns appearing in the multiple target individuals to be processed at each of the variant loci, from the variant information 40. In addition, the generator 18 generates the variant master table 28 from the extraction result of the variant patterns, the variant master table 28 being a table in which the positions of the storage regions for each of the variant loci in the variant storage data 100 and the correlation between the pattern numbers at each of the variant loci and the codes stored in the storage regions are registered. Then, the generator 18 generates the variant storage data 100 of each individual based on the generated variant master table 28. In this case, unlike the case where the generation of the variant master table 28 and the generation of the variant storage data 100 are performed in parallel, there is no request to rewrite the generated variant storage data 100 due to appearance of a new variant pattern, and it may be possible to increase the speed of generating the variant storage data 100.

Furthermore, in the first embodiment, the generator 18 uses the code $(11)_B$ as the certain code. In addition, when the second variant locus satisfies r−1=3n and a variant pattern at the second variant locus is the final variant pattern among the r types of variant patterns, the generator 18 stores the code $(11)_B$ in all storage regions for the second variant locus. As a result, it is possible to set the number r of types of variant patterns expressible by the k 2-bit regions to 3k+1 and reduce the length of the variant storage data.

Moreover, in the embodiments described above, the first aggregator 20 aggregates for each of the storage region and each of the code of the multiple individual to be processed how many times the codes stored in each of the storage regions in the variant storage data 100 appears in all of the multiple individuals, from the variant storage data 100 of each of the individuals. In addition, the second aggregator 22 aggregates for each of the variant loci and each of the types of the variant patterns how many times the variant patterns in the multiple individuals appears at the variant loci, from the aggregate result in each storage region obtained by the first aggregator 20. Dividing the aggregate processing into the aforementioned aggregate processing by the first aggregator 20 and the aforementioned aggregate processing by the second aggregator 22 omits the request to access the variant master table 28 in the middle of the aggregate processing by the first aggregator 20, and it is possible to increase the speed of the aggregate processing.

Furthermore, in the first embodiment, the second aggregator 22 integrates, as the aggregate result of the second variant locus, the aggregate results in the multiple storage regions for the same second variant locus among the aggregate results for each of the storage regions. In addition, for the second variant locus satisfying r−1=3n, the second aggregator 22 sets the number of times of appearance of the final variant pattern to the value obtained by subtracting the sum of the numbers of times of appearance of the variant patterns other than the final variant pattern from the number of target individuals to be processed. Then, the second aggregator 22 converts the number of times of appearance of each code included in the aggregate result by the first aggregator 20 to the number of times of appearance of the corresponding variant pattern, based on the correlation between the pattern number and the code registered in the variant master table 28. How many times each variant pattern appears at each variant locus is thereby obtained from the aggregate result of the number of times of appearance of each code in each storage region in variant storage data 100.

Moreover, in the second embodiment described above, the generator 18 stores the same code as that in the specific storage region, in the first storage region(s) in front of which the specific storage region exists in the variant storage data 100, among the storage regions for the second variant locus. In addition, the generator 18 stores the code $(11)_B$ in the second storage region(s) behind which the specific storage region exists in the variant storage data 100. When the second variant locus satisfies r−1=3n and a variant pattern at the second variant locus is the (r−1)th, that is, final variant pattern, the generator 18 stores the code (11)B in all storage regions for the second variant locus. Hence, as in the first embodiment, it is possible to set the number r of types of variant patterns expressible by the k 2-bit regions to 3k+1 and reduce the length of the variant storage data.

Furthermore, in the second embodiment described above, the second aggregator 22 integrates the aggregate results in the multiple storage regions for the same second variant locus among the aggregate results in the storage regions, as the aggregate result of the second variant locus. In addition, the second aggregator 22 updates the number of times of appearance of each of the codes other than the code $(11)_B$ among the numbers of times of appearance of codes aggregated for the storage regions in front of which the storage region for the same second variant locus exists in the variant storage data 100, in the following way. Specifically, from the number of times of appearance of the code other than the code $(11)_B$, the number of times of appearance of the code other than the code $(11)_B$ aggregated for the closest storage region existing in front in the variant storage data 100 is subtracted. Then, the second aggregator 22 converts the number of times of appearance of each code included in the aggregate result by the first aggregator 20 to the number of time of appearance of the corresponding variant pattern, based on the correlation between the pattern number and the code registered in the variant master table 28. How many times each variant pattern appears at each variant locus is thereby obtained from the aggregate result of the number of times of appearance of each code in each storage region in variant storage data 100.

Note that the relationship between the variant patterns (pattern numbers) and the codes is not limited to those illustrated in FIG. 14 or FIG. 21. For example, a relationship in which the specific code is set for all corresponding storage regions 102 when the pattern number p is 0 may be employed. Moreover, a code other than $(11)_B$ may be assigned as the specific code. Furthermore, in the relationship illustrated in FIG. 21, the same code as that in the specific storage region is stored in the first storage region(s) in front of which the specific storage region exists in the variant storage data 100. However, the same code as that in the specific storage region may be stored in the second storage region(s) behind which the specific storage region exists in the variant storage data 100.

Moreover, the disclosed technique may be applied to organisms other than humans. Although the storage region has the length of 2 bits in the aforementioned description, the length of the storage region (fixed bit length) may be selected as appropriate depending on the number r of types of variant patterns at most of the variant loci in an organism to which the disclosed technique is applied. In addition, also when the disclosed technique is applied to humans, the length of the storage region (fixed bit length) is not limited to 2 bits and may be, for example, 3 bits or the like.

Moreover, in the aforementioned description, explanation is given of a mode in which the variant information processing program 70 being an example of the variant information processing program in the disclosed technique is stored (installed) in advance in the memory unit 56. However, the variant information processing program in the disclosed technique may be provided in a form recorded in a recording medium such as a CD-ROM, a DVD-ROM, and a memory card.

All of documents, patent applications, and technical standards described in the specification are incorporated herein by reference as in the case where the documents, patent applications, and technical standards are described to be specifically and individually incorporated by reference.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A variant information processing device for processing genetic information of a plurality of individuals, the variant information processing device comprising:
   a processor configured to create variant storage data, from variant information of each of a plurality of target individuals to be processed, the variant information including information of variant locus and variant pattern associated with the variant locus, the variant locus corresponding to a portion where the genetic information varies among the plurality of target individuals, the variant pattern corresponding to the genetic information of the portion,
   the variant storage data including an array region including a first storage region with a fixed bit length and a second storage region with the fixed bit length,
   the variant locus being a first variant locus when the number r of the variant patterns associated with the variant locus is equal to or smaller than the number s of types of codes, each of the codes being associated with a corresponding one of the variant patterns and the first storage region configured to store the codes,
   the variant locus being a second variant locus when the number r of the variant patterns associated with the variant locus is greater than the number s,
   one of the codes associated with the variant pattern of the first variant locus being stored in the first storage region associated with the first variant locus, and
   another of one of the codes associated with the variant pattern of the second variant locus being stored in a specific storage region selected from between a portion of the first storage region associated with the second variant locus and the second storage region.

2. The variant information processing device according to claim 1, wherein the processor is further configured to
   extract all types of variant patterns for the target individuals at variant loci based on the variant information,
   create, from the extracted all types of variant patterns, a table in which positions of the storage regions for the variant loci in the variant storage data and a correlation between the types of variant patterns at the variant locus and the codes to be stored in the storage region are registered, and generate the variant storage data of each of the target individuals based on the created table.

3. The variant information processing device according to claim 2, wherein the processor is further configured to obtain a first aggregate result by aggregating the number of codes stored in each of storage regions of the variant storage data in all of the target individuals by the each of the storage regions and the each of the codes, based on the first aggregate result, aggregating the number of variant patterns of each of the types of the variant patterns of the target individuals.

4. The variant information processing device according to claim 3, wherein the processor is further configured to use a specific code set as the certain code in advance, when the second variant locus satisfies $(r-1)=n\times(s-1)$ and the variant pattern at the second variant locus is a specific variant pattern among the r types of variant patterns, store the specific code in all the storage regions for the second variant locus, and convert the number of codes included in the aggregate results included in the first aggregate result into the number of variant patterns corresponding to the codes, based on the correlation registered in the table, by setting the number of the specific variant patterns, for the second variant locus satisfying $(r-1)=n\times(s-1)$, at a value obtained by subtracting the sum of the numbers of the variant patterns other than the specific variant pattern from the number of the target individuals.

5. The variant information processing device according to claim 3, wherein the processor configured to store a code stored in the specific storage region, as a certain code, in a third storage region which is any of the storage regions for the second variant locus and on a first side of which the specific storage region exists in the variant storage data;

store a specific code set as the certain code in advance in a fourth storage region which is any of the storage regions for the second variant locus and on a second side of which the specific storage region exists in the variant storage data, the second side being opposite to the first side; and when the second variant locus satisfies $(r-1)=n\times(s-1)$ and the variant pattern at the second variant locus is a specific variant pattern among the r types of variant patterns, store the specific code in all the storage regions for the second variant locus, and convert the number of codes included in the aggregate results included in the first aggregate result into the number of variant patterns corresponding to the codes, based on the correlation registered in the table, by setting, for the number of times of appearance of a code other than the specific code among the numbers of codes aggregated for first one of the storage regions for the second variant locus on the first side of which a second one or more of the storage regions for the second variant locus exists in the variant storage data, as an aggregate result at the second variant locus, a value obtained by subtracting, from the number of codes other than the specific code aggregated for the first storage region, the number of codes other than the specific code aggregated for the closest second storage region on the first side.

6. The variant information processing device according to claim 1, wherein the processor is further configured to store a specific code set as a certain code in advance in all the storage regions for the second variant locus when the second variant locus satisfies $(r-1)=n\times(s-1)$ and the variant pattern at the second variant locus is a specific variant pattern among the r types of variant patterns.

7. The variant information processing device according to claim 1, wherein the processor is configured to store the code stored in the specific storage region as a certain code in a third storage region, the third storage region being any of the storage regions for the second variant locus and on a first side of the specific storage region when the storage regions are arranged in a line, store a specific code determined in advance as a certain code in a fourth storage region, the fourth storage region being any of the storage regions for the second variant locus and on a second side opposite to the first side relative to the specific storage region when the storage regions are arranged in the line, or store the specific code in the all storage regions for the second variant locus when the second variant locus satisfies $(r-1)=n\times(s-1)$ and the variant pattern at the second variant locus is a specific variant pattern among the r types of variant patterns.

8. The variant information processing device according to any one of claim 1, wherein the processor configured to add $INT((r-1)/(s-1))$ storage regions behind the array for the second variant locus satisfying $(r-1)\neq n\times(s-1)$, where $INT(x)$ is the nearest integer to which x is rounded down and n is a natural number, add $((r-1)/(s-1))-1$ storage regions behind the array for the second variant locus satisfying $(r-1)=n\times(s-1)$.

9. The variant information processing device according to claim 1, wherein the fixed bit length is 2 bits.

10. A variant information processing method for processing genetic information of a plurality of individuals, the variant information processing method comprising:

creating variant storage data, by a processor, from variant information of each of a plurality of target individuals to be processed, the variant information including information of variant locus and variant pattern associated with the variant locus, the variant locus corresponding to a portion where the genetic information varies among the plurality of target individuals, the variant pattern corresponding to the genetic information of the portion, the variant storage data including an array region including a first storage region with a fixed bit length and a second storage region with the fixed bit length, the variant locus being a first variant locus when the number r of the variant patterns associated with the variant locus being is equal to or smaller than the number s of types of codes, each of the codes being associated with a corresponding one of the variant patterns and the first storage region configured to store the codes, the variant locus being a second variant locus when the number r of the variant patterns associated with the variant locus is greater than the number s, one of the codes associated with the variant pattern of the first variant locus being stored in the first storage region associated with the first variant locus, the code associated with the variant pattern of the second variant locus being stored in a specific storage region selected from between the first storage region associated with the second variant locus and the second storage region, a certain code being stored, except the specific storage region, in the first storage region associated with the second variant locus or the second storage region.

11. The variant information processing method according to claim 10, wherein
extracting all types of variant patterns for the target individuals at variant loci based on the variant information,
creating, from the extracted all types of variant patterns, a table in which positions of the storage regions for the variant loci in the variant storage data and a correlation between the types of variant patterns at the variant locus and the codes to be stored in the storage region are registered, and
generating the variant storage data of each of the target individuals based on the created table.

12. The variant information processing method according to claim 11, wherein
obtaining a first aggregate result by aggregating the number of codes stored in each of storage regions of the variant storage data in all of the target individuals by the each of the storage regions and the each of the codes,
based on the first aggregate result, aggregating the number of variant patterns of each of the types of the variant patterns of the target individuals.

13. The variant information processing method according to claim 12, the method further comprising:
using a specific code set as the certain code in advance, when the second variant locus satisfies (r−1)=n×(s−1) and the variant pattern at the second variant locus is a specific variant pattern among the r types of variant patterns, and storing the specific code in all the storage regions for the second variant locus, and
converting the number of codes included in the aggregate results included in the first aggregate result into the number of variant patterns corresponding to the codes, based on the correlation registered in the table, by setting the number of the specific variant patterns, for the second variant locus satisfying (r−1)=n×(s−1), at a value obtained by subtracting the sum of the numbers of the variant patterns other than the specific variant pattern from the number of the target individuals.

14. The variant information processing method according to claim 12, wherein
storing a code stored in the specific storage region, as a certain code, in a third storage region which is any of the storage regions for the second variant locus and on a first side of which the specific storage region exists in the variant storage data;
storing a specific code set as the certain code in advance in a fourth storage region which is any of the storage regions for the second variant locus and on a second side of which the specific storage region exists in the variant storage data, the second side being opposite to the first side, and
when the second variant locus satisfies (r−1)=n×(s−1) and the variant pattern at the second variant locus is a specific variant pattern among the r types of variant patterns, storing the specific code in all the storage regions for the second variant locus, and
converting the number of codes included in the aggregate results included in the first aggregate result into the number of variant patterns corresponding to the codes, based on the correlation registered in the table, by setting, for the number of times of appearance of a code other than the specific code among the numbers of codes aggregated for first one of the storage regions for the second variant locus on the first side of which a second one or more of the storage regions for the second variant locus exists in the variant storage data, as an aggregate result at the second variant locus, a value obtained by subtracting, from the number of codes other than the specific code aggregated for the first storage region, the number of codes other than the specific code aggregated for the closest second storage region on the first side.

15. The variant information processing method according to claim 10, wherein
storing a specific code set as the certain code in advance in all the storage regions for the second variant locus when the second variant locus satisfies (r−1)=n×(s−1) and the variant pattern at the second variant locus is a specific variant pattern among the r types of variant patterns.

16. The variant information processing method according to claim 10, wherein
storing the code stored in the specific storage region as a certain code in a third storage region, the third storage region being any of the storage regions for the second variant locus and on a first side of the specific storage region when the storage regions are arranged in a line,
storing a specific code determined in advance as the certain code in a fourth storage region, the fourth storage region being any of the storage regions for the second variant locus and on a second side opposite to the first side relative to the specific storage region when the storage regions are arranged in the line, or
storing the specific code in the all storage regions for the second variant locus when the second variant locus satisfies (r−1)=n×(s−1) and the variant pattern at the second variant locus is a specific variant pattern among the r types of variant patterns.

17. The variant information processing method according to claim 10, wherein
adding INT((r−1)/(s−1)) storage regions behind the array for the second variant locus satisfying (r−1)≠n×(s−1), where INT(x) is the nearest integer to which x is rounded down and n is a natural number,
adding ((r−1)/(s−1))−1 storage regions behind the array for the second variant locus satisfying (r−1)=n×(s−1).

18. The variant information processing method according to any one of claim 10, wherein the fixed bit length is 2 bits.

19. A non-transitory computer-readable recording medium having stored therein a program for causing a computer to execute a process for a variant information processing for processing genetic information of a plurality of individuals, the process comprising:
creating variant storage data, from variant information of each of a plurality of target individuals to be processed, the variant information including information of variant locus and variant pattern associated with the variant locus, the variant locus corresponding to a portion where the genetic information varies among the plurality of target individuals, the variant pattern corresponding to the genetic information of the portion, the variant storage data including an array region including a first storage region with a fixed bit length and a second storage region with the fixed bit length, the variant locus being a first variant locus when the number r of the variant patterns associated with the variant locus is equal to or smaller than the number s of types of codes, each of the codes being associated with a corresponding one of the variant patterns and the first storage region configured to store the codes, the variant locus being a second variant locus when the number r of the variant patterns associated with the variant locus is greater than the number s, the code associated with the variant pattern of the first variant locus being stored in the first storage region associated with the first variant locus, the code associated with the variant pattern of the second variant locus being stored in a specific storage region selected from between the first storage region associated with the second variant locus and the second storage region, a certain code being stored, except the specific storage region, in the first storage region associated with the second variant locus or the second storage region.

* * * * *